(12) United States Patent
Coen et al.

(10) Patent No.: US 7,132,231 B2
(45) Date of Patent: Nov. 7, 2006

(54) FLUORESCENCE POLARIZATION METHOD FOR DETERMINING VIRAL INHIBITORS

(75) Inventors: Donald M. Coen, Medfield, MA (US); Beatrice D. Pilger, Zurich (CH)

(73) Assignee: President and Fellows of Harvard College, Cambridge, MA (US)

( * ) Notice: Subject to any disclaimer, the term of this patent is extended or adjusted under 35 U.S.C. 154(b) by 204 days.

(21) Appl. No.: 10/712,785

(22) Filed: Nov. 13, 2003

(65) Prior Publication Data

US 2005/0032245 A1   Feb. 10, 2005

Related U.S. Application Data

(63) Continuation of application No. PCT/US02/15878, filed on May 20, 2002.

(60) Provisional application No. 60/291,901, filed on May 18, 2001.

(51) Int. Cl.
*C12Q 1/00* (2006.01)
(52) U.S. Cl. .............................. 435/4; 435/18; 435/69.2
(58) Field of Classification Search ..................... None
See application file for complete search history.

(56) References Cited

U.S. PATENT DOCUMENTS

| 5,223,391 A | 6/1993 | Coen et al. ..................... 435/5 |
| 6,162,931 A * | 12/2000 | Gee et al. .................... 549/223 |
| 6,207,397 B1 * | 3/2001 | Lynch et al. ................. 435/7.8 |

FOREIGN PATENT DOCUMENTS

WO   WO 00/68185   11/2000

OTHER PUBLICATIONS

Keating S, Marsters J, Beresini M, Ladner C, Zioncheck K, Clark K, Arellano F, Bodary S (Jun. 2000) Proceedings of SPIE 3913, 128-137 and title page.*
Bridges et al., "Secondary structure and structure-activity relationships of peptides corresponding to the subunit interface of herpes simplex virus DNA polymerase," *J. Biol. Chem.*, 275(1):472-478 (2000).
Bridges et al., "Identification of crucial hydrogen-bonding residues for the interaction of herpes simplex virus DNA polymerase subunits via peptide display, mutational, and calorimetric approaches," *J. Virol.*, 75(11):4990-4998 (2001).
Chow and Coen, "Mutations that specifically impair the DNA binding activity of the herpes simplex virus protein UL42," *J. Virol.*, 69(11):6965-6971 (1995).
Coen et al., "Sensitivity of arabinosyladenine-resistant mutants of herpes simplex virus to other antiviral drugs and mapping of drug hypersensitivity mutations to the DNA polymerase locus," *J. Virol.*, 53(2):477-488 (1985).
Degterev et al., "Identification of small-molecule inhibitors of interaction between the BH3 domain and Bcl-xL," *Natl. Cell Biol.*, 3(2):173-182 (2001).
Digard and Coen "A novel functional domain of an alpha-like DNA polymerase. The binding site on the herpes simplex virus polymerase for the viral UL42 protein," *J. Biol. Chem.*, 265(29):17393-17396 (1990).
Digard et al., "Functional analysis of herpes simplex virus UL42 protein," *J. Virol.*, 67:1159-1168 (1993).
Digard et al., "The extreme C terminus of herpes simplex virus DNA polymerase is crucial for functional interaction with processivity factor UL42 and for viral replication," *J. Virol.*, 67(1):398-406 (1993).
Digard et al., "Specific inhibition of herpes simplex virus DNA polymerase by helical peptides corresponding to the subunit interface," *Proc. National. Acad. Sci. U SA.*, 92:1456-1460 (1995).
Digard et al., "Mutational analysis of DNA polymerase substrate recognition and subunit interactions using herpes simplex virus as prototype," *Methods Enzymol.*, 262:303-322 (1995).
Gottlieb et al., "The Herpes Simplex Virus Type 1 UL42 Gene Product; a Subunit of DNA Polymerase that Functions to Increase Processivity," *J. Virol.*, 64(12):5976-5987 (1990).
Gottlieb and Challberg, "Interaction of herpes simplex virus type 1 DNA polymerase and the UL42 accessory protein with a model primer template," *J. Virol.*, 68(8):4937-4945 (1994).
Hamatake et al., "The herpes simplex virus type 1 DNA polymerase accessory protein, UL42, contains a functional protease-resistant domain," *J. Gen, Virol.*, 74 ( Pt 10):2181-2189 (1993).
Loregian et al., "Intranuclear delivery of an antiviral peptide mediated by the B subunit of *Escherichia coli* heat-labile enterotoxin," *Proc. Natl. Acad. Sci. USA.*, 96:5221-5226 (1999).
Marsden et al., "Role of the carboxy terminus of herpes simplex virus type 1 DNA polymerase in its interaction with UL42," *J. Gen. Virol.*, 75:3127-3135 (1994).
Pritchard and Stefano, "Amplified detection of viral nucleic acid at subattomole levels using Q beta replicase," *Ann. Biol. Clin.*, (Paris) 48(7):492-497 (1990).
Stow et al., "Inhibition of herpes simplex virus type 1 DNA replication by mutant forms of the origin-binding protein," *Virology*, 196:413-418 (1993).
Tenney et al., "Deletions of the carboxy terminus of herpes simplex virus type 1 UL42 define a conserved amino-terminal functional domain," *J. Virol.*, 67(4):1959-1966 (1993).
Tenney et al., "Mutations in the C terminus of herpes simplex virus type 1 DNA polymerase can affect bonding and stimulation by its accessory protein UL42 without affecting basal polymerase activity," *J. Virol.*, 67(1):543-547 (1993).

(Continued)

*Primary Examiner*—Ralph Gitomer
(74) *Attorney, Agent, or Firm*—Banner & Witcoff, Ltd.

(57) ABSTRACT

Methods for determining inhibitors of protein interactions are provided. The method involves evaluation of potential inhibitors that can inhibit or prevent protein interactions. The method provides for high-throughput identification of novel therapeutics that can treat a disease or disorder by inhibiting protein interactions.

14 Claims, 7 Drawing Sheets

OTHER PUBLICATIONS

Weisshart et al., "Structural and functional organization of herpes simplex virus DNA polymerase investigated by limited proteolysis," *J. Biol. Chem.*, 269(36):22788-22796 (1994).

Weisshart et al., "Herpes simplex virus processivity factor UL42 imparts increased DNA-binding specificity to the viral DNA polymerase and decreased dissociation from primer-template without reducing the elongation rate." *J. Virol.*, 73(1):55-66 (1999).

Zuccola et al., "The crystal structure of an unusual processivity factor, herpes simplex virus UL42, bound to the C terminus of its cognate polymerase," *Mol. Cell.*, 5:267-278 (2000).

* cited by examiner

FLUORESCENCE POLARIZATION METHOD FOR DETERMINING VIRAL INHIBITORS

RELATED APPLICATIONS

This application is a continuation of PCT application No. PCT/US02/15878, designating the United States and filed on May 20, 2002; which claims the benefit of U.S. Provisional Application No. 60/291,901 filed on May 18, 2001, the entire disclosures of which are incorporated herein by reference for all purposes.

STATEMENT OF GOVERNMENT INTERESTS

This invention was made with Government support under Grant Number AI26077 awarded by the National Institutes of Health. The Government has certain rights in the invention.

FIELD OF THE INVENTION

The present invention relates to methods and kits for screening potential inhibitors of protein interactions. More specifically, the present invention relates to screening of potential compounds to inhibit herpes simplex virus (HSV) DNA polymerase subunit interactions.

BACKGROUND OF THE INVENTION

The mechanism of action for many drugs is to inhibit one or more enzymes of an organism or cell involved in a disease or disorder. The vast majority of small-molecule pharmaceuticals act by inhibiting enzymes or membrane-bound receptors. These protein targets have naturally selected pockets that enable them to bind to small molecules, e.g. typically they bind small molecules at the active site of the enzyme. The increased use of current therapeutics, however, has led to constant emergence of drug resistant organisms.

Within the past few years it has become apparent that coordinated protein-protein interactions play a major role in cellular, viral or disease processes. However, the search for drugs that block protein-protein interactions has yet to be successful for wide range applications.

It is an object of the present invention to provide a method for identifying potential inhibitors which can treat a disorder by inhibiting, disrupting, or altering protein:protein interactions. In certain preferred embodiments, the method comprises identifying compounds that can inhibit herpes simplex virus by altering or disrupting the interaction between the catalytic subunit and the processivity subunit of herpes simplex virus DNA polymerase.

SUMMARY

Embodiments of the present invention are directed to methods for identifying compounds effective to dissociate, inhibit or otherwise interfere with protein binding interactions. Using the novel methods, one can identify compounds that can be used to inhibit the binding activity of certain proteins or protein subunits the binding of which are known to be causative of certain disease or viral conditions. Alternatively, promising lead candidate compounds can be identified by the present invention based upon an ability to interact with proteins or protein subunits known to bind to one another. Such compounds themselves can be therapeutically useful or they can serve as lead compounds to be further developed into pharmacologically active compounds or formulations.

According to the present invention, a test sample including a known binding pair of proteins or protein subunits including a fluorescent label is analyzed by fluorescence polarization. The test sample is then contacted with a candidate inhibitor compound and the fluorescence polarization is then determined. The ability of the compound to cause dissociation of or otherwise interfere with or prevent binding of the proteins or protein subunits is monitored by fluorescence polarization.

Embodiments of the present invention advantageously utilize a test sample including fragments of subunits of proteins known to bind to one another. The test sample includes at least a fragment of a first subunit and at least a fragment of a second subunit. The fragment of the first subunit and the fragment of the second subunit are capable of interacting to form a dimer and, according to one embodiment, when contacted within the sample, bind to one another. Either the fragment of the first subunit or the fragment of the second subunit includes a fluorescent label. The fluorescence polarization of the bound first and second subunits in the test sample is determined. At least one candidate test compound is then contacted with the test sample to form a test mixture. Fluorescence polarization of the test mixture is evaluated to determine if the test compound has disrupted interaction between, or otherwise interfered with binding between the fragment of the first subunit and the fragment of the second subunit. In accordance with one aspect, fluorescence polarization of the test mixture is compared to fluorescence polarization of the test sample. A decrease in the fluorescence polarization of the test mixture, when compared to the fluorescence polarization of the test sample, indicates the first fragment is no longer bound to the second fragment.

In accordance with an additional aspect, a method of testing compounds for inhibiting herpes simplex virus DNA polymerase subunit interactions is provided. The method includes providing a test sample which includes a peptide which is identical to or substantially homologous to an eighteen amino acid C-terminal fragment of catalytic unit of herpes simplex virus DNA polymerase. The C-terminal fragment of catalytic unit of herpes simplex virus DNA polymerase also includes a fluorescent label. The test sample further includes a functional fragment of processivity subunit of herpes simplex virus DNA polymerase. The test sample is combined with at least one test compound to form a test mixture. Fluorescence polarization of the test mixture is evaluated to determine if the test compound has disrupted or otherwise interfered with interaction of the C-terminal fragment and the functional fragment of processivity subunit. It will be recognized by those skilled in the art given the benefit of this disclosure that fluorescence polarization measurements can typically be correlated to the level of inhibition of the herpes simplex virus DNA polymerase.

In accordance with another aspect, a method for testing compounds to inhibit herpes simplex virus DNA polymerase subunits is provided. The method includes providing a test sample including a peptide including an amino acid sequence as shown in SEQ ID NO.:1 below. The peptide also includes a fluorescent label. The test sample further includes a protein fragment including an amino acid sequence as shown in SEQ ID NO.:2, and the peptide and the protein fragment are capable of interacting to form dimer. The test sample is combined with at least one test compound to form a test mixture. Fluorescence polarization of the test mixture is evaluated to determine if the at least one test compound has disrupted or otherwise interfered with interaction between the peptide and the protein fragment.

In accordance with another aspect, a kit for testing inhibitors of protein interactions is disclosed. The kit includes at least a first reagent which includes a fragment of a first subunit. The first reagent typically also includes a fragment of a second subunit. The fragment of the first subunit and the fragment of the second subunit are capable of interacting to form a dimer. The fragment of the first subunit also includes a fluorescent label.

In accordance with an additional aspect, a kit for testing compounds for inhibiting herpes simplex virus is disclosed. The kit includes at least a first reagent which includes a peptide that is identical to or substantially homologous to an eighteen amino acid C-terminal fragment of the catalytic unit of herpes simplex virus DNA polymerase. The C-terminal fragment also typically includes a fluorescent label. The first reagent typically also includes a fragment of processivity subunit of herpes simplex virus DNA polymerase. According to one embodiment, the reagent includes a peptide which includes an amino acid sequence as shown in SEQ ID NO.:1 and a protein fragment which includes an amino acid sequence as shown in SEQ ID NO.:2.

In accordance with an additional aspect, a composition for treating herpes simplex virus is disclosed. The composition includes a compound of formula I, or pharmaceutically suitable salt or solvate thereof.

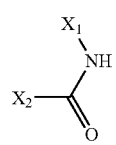

(I)

in which $X_1$ preferably is

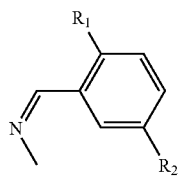

in which $X_2$ preferably is

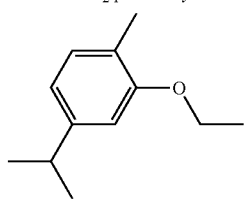

and in which each of $R_1$ and $R_2$ may be any of the following: —$NO_2$, —$NH_2$, —OH, —COOH, —Cl, —Br, —I, or —O—X, where X is a saturated or unsaturated hydrocarbon including 1–8 carbon atoms. In certain embodiments, the compound is BP1 (as shown in FIG. 2 below), or a pharmaceutically suitable salt or solvate thereof.

In accordance with another aspect, a composition for treating herpes simplex virus is disclosed. The composition includes a compound of formula II, or pharmaceutically suitable salt or solvate thereof.

(II)

Preferably $X_1$ is 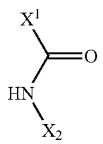

And $X_2$ is 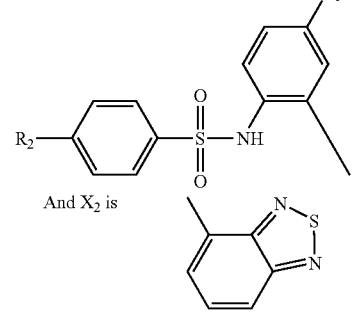

Preferably $R_1$ and $R_2$ each are selected from the following: —$NO_2$, —$NH_2$—OH, —COOH, —Cl, —Br, —I, and —O—X, where X is a saturated or unsaturated hydrocarbon including 1–8 carbon atoms. In certain embodiments, the compound is BP5 (as shown in FIG. 2 below), or a pharmaceutically suitable salt or solvate thereof.

In accordance with an additional aspect, a method of treating herpes simplex virus in a mammal, e.g. a human, is provided. The method includes administering a pharmaceutically effective amount, e.g. an efficacious amount, of a compound of formula I or formula II, or pharmaceutically suitable salts or solvates thereof, to the mammal.

It will be recognized by those skilled in the art given the benefit of this disclosure, that certain preferred embodiments of the present invention provide for high-throughput testing of potential inhibitors of protein interactions. The robust methods and kits disclosed here can be employed to test large libraries of compounds in a rapid and cost-effective manner to develop therapeutics which target, e.g. inhibit, protein interactions.

BRIEF DESCRIPTION OF THE FIGURES

The patent or application file contains at least one drawing executed in color. Copies of this patent or patent application publication with color drawing will be provided by the Office upon request and payment of the necessary fee.

Certain preferred embodiments of the present invention will be described below with reference to the accompanying figures in which.

DETAILED DESCRIPTION OF CERTAIN PREFERRED EMBODIMENTS

Figure 1:
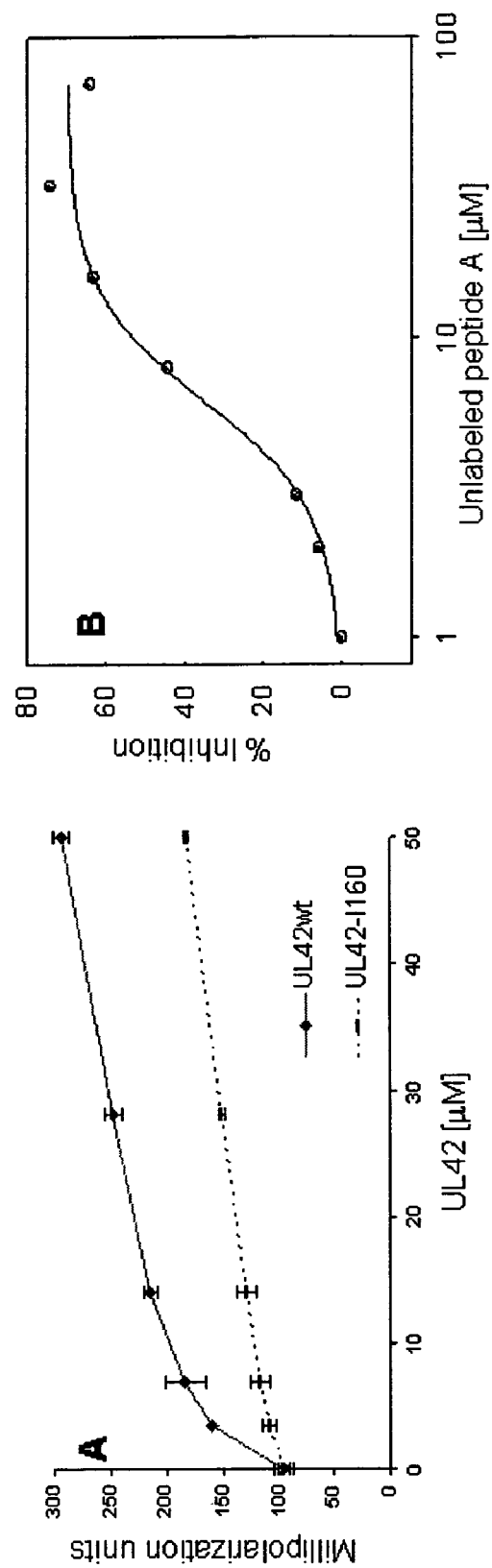
FIG. 1. shows testing of fragments of protein subunits in accordance with certain preferred embodiments.

It is a significant advantage that the methods and kits disclosed herein provide for screening of compounds that can dissociate, disrupt, inhibit or otherwise interfere with binding interactions between proteins or protein subunits or fragments thereof. Inhibition of such protein interactions can provide for treatment of numerous disorders by halting growth or metabolic functions of the disease causing organisms. Such testing can lead to drug candidates for treating the disease or disorder in which the protein is involved. Though the examples disclosed here are generally directed towards testing of inhibitors of viral DNA polymerases, one skilled in the art given the benefit of this disclosure will be readily able to adapt the methods disclose herein for these and other intended uses. For example, even though the methods disclosed herein are suitable for identifying compounds which can inhibit protein interactions to inhibit activity of the protein, the methods are equally applicable to disruption of protein interactions to activate a protein. For example, in equation I below interaction of subunits $A_1$ and $B_1$ results in an active protein. When this interaction is disrupted by inhibitor 1 ($I_1$), the subunits dissociate and the protein is rendered inactive, e.g. activity is inhibited.

Eqn. I

In contrast, in equation II below, interaction of subunits $A_2$ and $B_2$ results in an inactive protein. When this interaction is disrupted by inhibitor 2 ($I_2$) the subunits dissociate and the protein becomes active.

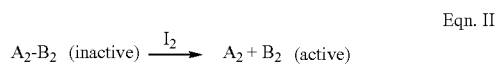

Eqn. II

Accordingly, the methods disclosed here are equally applicable to identification of compounds which disrupt protein interactions to inhibit activity of a functional protein and to identification of compounds which disrupt protein interactions to promote activity of a functional protein. However, it will be within the ability of those skilled in the art given the benefit of this disclosure to use the methods disclosed herein for these and other uses.

The following terms are intended to have the following meanings unless otherwise clear from the context of usage.

As used here "protein interaction" or "protein:protein interaction" refers to the interaction of different subunits, or portions or fragments thereof, of a protein. That is, protein interaction refers to the interaction between at least a portion of two subunits which comprise a functional protein. In certain embodiments, protein interaction refers to an interaction between two or more distinct proteins which interact to form a functional and/or non-function protein. For example, in embodiments where a first protein interacts with a second protein to inhibit the activity of the second protein (or activate the second protein as the case may be), the protein interaction typically occurs through weak forces, such as hydrogen bonding, salt bridges, Van der Waals forces, London dispersion forces and the like. Preferably, the protein interaction is reversible such that dissociation of the proteins, or protein subunits, can occur under suitable conditions. Preferably, such forces are weak, e.g. have $K_d$'s in the μM range, such that a compound having suitable properties can disrupt the interaction between the two subunits. As used here "disrupt" refers to breaking of, weakening of or interfering with, as the case may be, the interactions between the fragments and/or subunits in the test sample.

As used here "test sample" refers to a sample comprising two or more proteins, peptides or fragments thereof (collectively, "fragments") which can interact under suitable conditions. That is, the fragments have the ability to interact with each other, e.g. through Van der Waals interactions, hydrogen bonds, hydrophobic interactions, and the like, under suitable conditions. In certain preferred embodiments, the fragments can interact to form a functional protein, or a functional portion of a protein. For example, in the case of many viral polymerases, a fragment of a catalytic subunit (or the entire catalytic subunit as the case may be) can interact with a fragment of processivity subunit (or the entire processivity subunit as the case may be) to form a functional protein, e.g. a functional polymerase capable of synthesizing viral DNA. It will be understood by those skilled in the art given the benefit of this disclosure that a sample, aliquot or portion of the test sample can be used to form test mixtures. That is, the entire test sample need not be combined with a test compound to form the test mixture, but, instead, only a suitable volume of test sample is necessary.

As used here "at least one test compound" refers to one or more compounds which have the potential of disrupting protein interactions. The test compound preferably is dissolved in a suitable solvent, e.g. buffer, such that the test compound can be added to the test sample to form a test mixture. In accordance with certain preferred embodiments, the test compounds may be selected based on numerous criteria, such as, for example, solubility, physical properties, structural similarity to compounds which are known or thought to be inhibitors of protein interactions, etc. In certain embodiments, the compounds are randomly selected from a library, e.g. a combinatorial library, and tested using the methods disclosed here. Suitable methods for synthesizing combinatorial libraries are known to those skilled in the art, and suitable combinatorial library members for testing using the methods disclosed here will be readily apparent to those skilled in the art given the benefit of this disclosure. Preferably, the number of members of the library is high, e.g. $10^2$, $10^3$, $10^4$, $10^5$, $10^6$, $10^7$ or greater. In certain preferred embodiments, the test compounds are assayed individually to determine if the compound can inhibit protein interactions. In other embodiments, the test compounds are assayed in groups to determine if any member of the group can inhibit protein interactions. Such group testing allows for removal of large groups of compounds that do not inhibit protein interactions. For example, a group comprising 100 members of a library which does not inhibit protein interactions allows for elimination of all 100 members of the group in a single assay, whereas individual testing of the compounds would require 100 separate assays. One skilled in the art given the benefit of this disclosure will be able to design suitable assays for testing large numbers of compounds using the methods disclosed here.

In accordance with certain preferred embodiments, the test compounds are evaluated for their ability to inhibit protein interactions by measuring fluorescence polarization of the test mixture(s). Without wishing to be bound by any particular scientific theory, fluorescence polarization measurements allow for discrimination between fluorescently labeled bound and unbound proteins, peptides, subunits or fragments thereof, for example the first labeled fragment and the second fragment. Again without wishing to be bound by any particular scientific theory, the fluorescence polarization of the fluorescently labeled first fragment of first subunit is small because the fluorescently labeled first fragment rotates rapidly in solution and, therefore, has randomized photoselected distributions which result in the small observed fluorescence polarization. When the fluorescently labeled first fragment of the first subunit interacts with the fragment of the second subunit, which typically is a larger more slowly rotating molecule, the rotation of the fluorescently labeled first fragment slows and the fluorescence polarization increases dramatically. Accordingly, disruption of the subunit interaction by a test compound provides a decrease in the fluorescence polarization which is indicative of inhibition of the protein interactions. One skilled in the art given the benefit of this disclosure will be able to evaluate test compounds for their ability to disrupt protein:protein interaction using the methods disclosed herein.

In accordance with certain preferred embodiments, the fluorescence polarization measurements in the presence of at least one test compound can be compared with the fluorescence polarization measurements in the absence of the test compound. Depending on the assay method selected, such comparison can be made manually by the operator, e.g. by subtraction, or can be made automatically by a computer, for example. In certain preferred embodiments where high-throughput assays are used, using a 384 well plate, for example, one or more wells, or positions in an array, for example, may comprise only a sample of test sample to provide a reference or baseline for the measurements. These wells can act as a baseline for which all other wells, each of which may comprise a test mixture, can be compared. Accordingly, a difference in fluorescence polarization between the wells comprising test sample and wells comprising test mixture indicates that the test compound has disrupted the protein interactions in some manner. For example, when a test compound disrupts the interaction between fluorescently labeled first fragment of the first subunit and first fragment of second subunit, the fluorescence polarization typically decreases as the fluorescently labeled first fragment of the first subunit dissociates, e.g. stops interacting with, from the first fragment of second subunit. One skilled in the art given the benefit of this disclosure will be able to select suitable methods for comparing the fluorescence polarization of a test mixture with fluorescence polarization of a reference sample.

In accordance with certain preferred embodiments, at least one of the fragments of the test mixture typically includes a fluorescent label. The fluorescent label typically can be any fluorescent label which can be attached to a fragment, and preferably the fluorescent label is attached to a smaller fragment. Preferably, the fluorescent label does not interfere with the interaction between the fragments and/or subunits. That is, preferably the fluorescent label does not alter the interaction between the components of the test sample, e.g. the first subunit and the second subunit. In certain preferred embodiments, the fluorescent label has a high quantum yield, e.g. greater than 0.5, more preferably greater than 0.75 and most preferably greater than 0.9, such that fluorescence measurements can be readily made. In certain preferred embodiments, the fluorescent label is selected from pentafluorofluorescein-derivative Oregon Green 514, Oregon Green 488, BODIPY fluorescent dye, tetramethylrhodamine dyes (each from Molecular Probes), and other labels suitable for performing fluorescence polarization measurements. Other suitable labels will be readily apparent to those skilled in the art given the benefit of this disclosure.

As used here "test mixture" refers to the combination of at least one test compound and the test sample or portion or aliquot thereof. The test mixture may further comprise other suitable components, e.g. buffers, salts, organic solvents, proteins and the like, to facilitate protein interactions and/or evaluation of the test mixture. In accordance with certain preferred embodiments, the test mixture used in the method disclosed here typically is formed by adding at least one test compound to a test sample. One skilled in the art given the benefit of this disclosure will recognize that a sample of the test sample could be added to the test compound to form a test mixture. That is, as long as the test sample and the test compound are combined, e.g. placed in the same solution, a test mixture suitable for performing the methods disclosed here will be formed. The test compound can be added to a sample of the test sample using numerous methods and apparatus. In embodiments comprising assays performed in test tubes or Eppendorf tubes, for example, the test compound can be added using conventional techniques such as a syringe, pipette, micropipette and the like, for example. In embodiments comprising high-throughput assays, the test compound(s) is preferably added using automated techniques, such as autoloaders, automatic pipettes, or arrays, for example. In certain preferred embodiments, a multi-well plate, e.g. a plate having 96 or 384 wells, is used to test a plurality of samples simultaneously. Use of a multi-well plate, along with a plate reader which is configured to read a plurality of the wells in a rapid manner, allows a significant number of test compounds to be assayed efficiently and rapidly for their ability to inhibit protein interactions by using the methods disclosed here. In certain embodiments, a plurality of test compounds are fixed in an array and a test sample is added to each position on the array. Such arrays provide for high-throughput testing of a plurality of test compounds. One skilled in the art given the benefit of this disclosure will be able to design suitable high-throughput assays for testing a large number of test compounds.

As used here "SEQ ID NO.: 1" refers to the following amino acid sequence: Ac-Ala-Thr-Ala-Glu-Glu-Glu-Thr-Arg-Arg-Met-Leu-His-Arg-Ala-Phe-Asp-Thr-Leu-Ala-$NH_2$, which is also referred to in the Example as peptide E. The amino acid sequence of peptide E (SEQ ID NO.:1) can be found in Digard P, Williams KP, Hensley P, Brooks IS, Dahl CE, Coen DM. "Specific inhibition of herpes simplex virus DNA polymerase by helical peptides corresponding to the subunit interface. Proc Natl Acad Sci USA 1995; 92:1456–1460," and also in Bridges K G, Hua Q, Brigham-Burke M R, Martin J D, Hensley P, Dahl C E, Digard P, Weiss M A, Coen D M. "Secondary structure and structure-activity relationships of peptides corresponding to the subunit interface of herpes simplex virus DNA polymerase." J Biol Chem 2000; 274:472–478. SEQ ID NO.:2, which corresponds to the amino acid sequence for UL42Δ340 mutant of the processivity subunit of HSV DNA polymerase, which is described on page 4991 of Bridges K G, Chow C S, Coen D M. "Identification of crucial hydrogen-bonding residues for the interaction of herpes simplex virus DNA polymerase subunits via peptide display, mutational, and calorimetric approaches." J Virol 2001; 75:4990–4998, is shown in Table 4. SEQ ID NO.:3, which corresponds to the amino acid sequence of the catalytic subunit of HSV DNA polymerase, which can be found at http://www.stdgen.lanl.gov/cgi-bin/gene_id_search.cgi?dbname=hhv1&gene_id=HHVONE033, and SEQ ID NO.:4, which corresponds to the amino acid sequence for UL42, which can be found at http://www.stdgen.lanl.gov/cgi-bin/gene_id_search.cgi?dbname=hhv1&gene_id=HHVONE045, are also shown below in Table 4.

As used here "pharmaceutically suitable salt" refers to salts of compounds which are suitable for administration to a mammal, e.g. a human, for treating a disorder. For example, in embodiments where one or more nitrogen groups are present, chloride and hydrochloride salts may be pharmaceutically suitable salts. In embodiments where one or more carboxyl groups are present, alkali metal salts, e.g. sodium and potassium, may be pharmaceutically suitable salts. One skilled in the art given the benefit of this disclosure will be able to select suitable pharmaceutically suitable salts depending on the use and on the properties of the compound.

As used here "solvate" refers to an aggregate that comprises one or more molecules of the solute, such as a suitable amount of compound I, for example, with one or more molecules of a suitable solvent.

As used here "suitable solvent" refers to a solvent which sufficiently solubilizes one or more molecules of the solute to effect the desired result.

In accordance with certain preferred embodiments, a method is provided, in which the method includes providing a test sample which includes at least a fragment of a first subunit and at least a fragment of a second subunit. The fragment of the first subunit and the fragment of the second subunit are capable of interacting to form a dimer. The fragment of the first subunit includes a fluorescent label. The test mixture is formed by combining at least one test compound and a test sample. Fluorescence polarization of the test mixture is evaluated to determine if the test compound has disrupted interaction between the fragment of the first subunit and the fragment of the second subunit. In certain preferred embodiments, the fragments of first subunit and second subunit typically can be any size, e.g. any number of amino acids, as long as the fragments are capable of forming a dimer. In certain embodiments, the first fragment is a portion of a protein, e.g. a peptide. Preferably the first fragment of the first subunit is small enough such that a difference in fluorescence polarization can be observed when the first fragment of the first subunit and the first fragment of the second fragment interact. That is, the first fragment of the first subunit can generally be any size that is suitable for performing fluorescence polarization measurements which allow a distinction between first fragment of the first subunit which is free in solution and first fragment of the first subunit which is interacting with first fragment of the second subunit. Preferably, the first fragment of the first subunit comprises no more than about 40 amino acids, more preferably no more than about 30 amino acids and most preferably no more than about 20 amino acids, e.g. 18 amino acids or less. More preferably, the first fragment of the first subunit is a peptide which includes an amino acid sequence as shown in SEQ ID NO.: 1. According to one embodiment, the first fragment of the first subunit is substantially identical to that shown in SEQ ID NO.: 1. Preferably, the first fragment of the second subunit is substantially larger than the first fragment of the first subunit such the interaction of fluorescently labeled first fragment of the first subunit with the first fragment of the second subunit results in an increase in fluorescence polarization. More preferably, the first fragment of the second subunit comprises a protein which includes an amino acid sequence of either SEQ ID NO.: 2 or SEQ ID NO.:4. However, as discussed above, as long as a distinction can be made between free and interacting first fragment of the first subunit, the first fragment of the first subunit and the first fragment of the second subunit may comprise any number of amino acids. Depending on the nature and characteristics of the subunit interaction, the sizes of the fragments can vary. One skilled in the art given the benefit of this disclosure will be able to select and design suitable subunit fragments for use in the methods disclosed here.

In accordance with a certain preferred embodiments, a method is disclosed in which the method includes providing a test sample which includes a first fragment of a protein subunit bound to a second fragment of protein subunit. Preferably, the first fragment of protein subunit includes a fluorescent label. The method further includes measuring fluorescence polarization of the test sample. At least one test compound and the test sample are combined to form a test mixture, and fluorescence polarization of the test mixture is measured. The fluorescence polarization of the test mixture and the fluorescence polarization of the test sample are compared. A decrease in the fluorescence polarization of the test mixture, when compared to the fluorescence polarization of the test sample, indicates the first fragment is no longer bound to the second fragment. In certain preferred embodiments, the first and second fragments of protein subunit typically can be any size, e.g. any number of amino acids, as long as the fragments are capable of binding to form a dimer. In certain embodiments, the first and second fragments each are portions of a protein, e.g. a peptide. Preferably the first fragment of the protein subunit is small enough such that a difference in fluorescence polarization can be observed when the first fragment and second fragment bind. That is, the first fragment of the protein subunit can generally be any size that is suitable for performing fluorescence polarization measurements which allow a distinction between first fragment of protein subunit which is free in solution and first fragment of protein subunit which is bound to the second first fragment of the protein subunit. Preferably, the first fragment of the first subunit comprises no more than about 40 amino acids, more preferably no more than about 30 amino acids and most preferably no more than about 20 amino acids, e.g. 18 amino acids or less. More preferably, the first fragment is a peptide which includes an amino acid sequence as shown in SEQ ID NO.: 1. According to one embodiment, the first fragment is substantially identical to that shown in SEQ ID NO.: 1. Preferably, the second fragment is substantially larger than the first fragment such that interaction of fluorescently labeled first fragment with the second fragment results in an increase in fluorescence polarization. More preferably, the second fragment includes a protein which includes an amino acid sequence as shown in SEQ ID NO.:2 or SEQ ID NO.:4. However, as discussed above, as long as a distinction can be made between free and bound first fragment, the first and second fragments may comprise any number of amino acids. In certain embodiments, the fragments comprise only the minimal number of amino acids necessary for successful protein interaction. Thus, depending on the nature and characteristics of the fragment interactions, the sizes of the fragments can vary. One skilled in the art given the benefit of this disclosure will be able to select and design suitable subunit fragments for use in the methods disclosed here.

In accordance with certain preferred embodiments, a method of testing compounds for inhibiting herpes simplex virus DNA polymerase subunit interactions is disclosed. The method includes providing a test sample which includes a peptide which is substantially homologous to an eighteen amino acid C-terminal fragment of catalytic unit of herpes simplex virus DNA polymerase. The C-terminal fragment of catalytic unit of herpes simplex virus DNA polymerase typically includes a fluorescent label. The test sample also includes a functional fragment of processivity subunit of herpes simplex virus DNA polymerase. At least one test compound and the test sample are combined to form a test mixture, and fluorescence polarization of the test mixture is evaluated. In certain embodiments, the decrease in fluorescence polarization can be correlated to the level of DNA synthesis inhibition That is, the fluorescence polarization of the test mixture can be compared with the fluorescence polarization of the test sample to determine if there is any difference in fluorescence polarization. If such a difference is observed, the degree of difference can be correlated as a measure of the ability of the test compound to disrupt protein interactions. The herpes simplex virus (HSV) DNA polymerase is a heterodimer consisting of a catalytic (Pol) and a processivity (UL42) subunit. The interaction of these subunits is crucial for the synthesis of long-chain DNA products and for viral replication, representing an attractive target for antiviral drug discovery. This processivity factor allows Pol to synthesize extended stretches of DNA without dissociating from the template [Gottlieb et al. 1990; Gottlieb et al. 1994; Weisshart et al. 1999]. The residues necessary for the specific interaction with UL42 lie at the extreme C-terminus of Pol [Weisshart et al. 1994; Marsden et al. 1994; Digard et al. 1993; Tenney et al. 1993; Stow et al. 1993; Digard et al. 1990]. Recent work in our laboratory [Bridges et al. 2001] including the crystal structure of UL42 with the bound Pol-peptide [Zuccola et al. 2000] clarified the important residues of the other binding partner, UL42, and explained previous findings [Chow et al. 1995]. It has been observed that peptides corresponding to the extreme C-terminus of Pol inhibit UL42 stimulated long chain DNA polymerization by Pol [Digard et al. 1995]. Synthetic peptides ranging from 36 amino acids (peptide A) down to an 18 amino acid truncated peptide (peptide E) corresponding to the C-terminus of Pol exhibit $IC_{50}$ values of 3 uM and 11 uM, respectively [Digard et al. 1995; Bridges et al. 2000] for specific inhibition of UL42 stimulated long-chain DNA synthesis. When a similar, 27-mer peptide is delivered into virally infected cells, it specifically interferes with HSV replication [Loregian et al. 1999].

In accordance with certain preferred embodiments, the peptide which is substantially homologous to an eighteen amino acid C-terminal fragment of catalytic unit of herpes simplex virus DNA polymerase is preferably at least about 90% homologous (in amino acid sequence), more preferably has a sequence homology of at least about 95% and most preferably has a sequence homology of at least about 99%. Determination of sequence homologies will be readily apparent to those skilled in the art given the benefit of this disclosure and exemplary methods include but are not limited to Swiss-PDB, sequence alignment algorithms, BLAST, etc. and the like. In certain preferred embodiments, the peptide has an amino acid sequence including SEQ ID NO.: 1. In certain preferred embodiments, the functional fragment of processivity subunit includes a protein which has an amino acid sequence including SEQ ID NO.: 2.

In accordance with certain preferred embodiments, a functional fragment of processivity subunit of herpes simplex virus DNA polymerase comprises a fragment of the processivity subunit which retains substantially all biochemical activities of the entire processivity subunit. For example, it has been shown that a truncated version of UL42 (UL42Δ340 having SEQ ID NO.: 2) that was expressed in BL21(de3)pLysS E.coli as maltose binding protein fusion as described [Bridges et al. 2001] and purified over an amylose column (New England Biolabs), retained all known biochemical activities of UL42 [Hamatake et al. 1993; Digard et al. 1993; Tenney et al. 1993] but unlike full-length UL42. Thus in certain embodiments, the functional fragment of processivity subunit may comprise the entire processivity subunit, whereas in other embodiments, the functional fragment of processivity subunit comprises a truncated version of the processivity subunit which retains all known biochemical activities of the full processivity subunit. In certain preferred embodiments, the functional fragment of processivity subunit of herpes simplex virus DNA polymerase includes an amino acid sequence as shown in SEQ ID NO.: 2. In certain preferred embodiments, the peptide which is substantially homologous to an eighteen amino acid C-terminal fragment of catalytic unit of herpes simplex virus DNA polymerase includes an amino acid sequence which includes SEQ ID NO.: 1 and the functional fragment of processivity subunit of herpes simplex virus DNA polymerase includes an amino acid sequence which includes SEQ ID NO. 2.

In accordance with certain preferred embodiments, a kit for testing inhibitors of protein interactions is disclosed. The kit includes at least a first reagent including a fragment of a first subunit and a fragment of a second subunit. The first fragment of the first subunit includes a fluorescent label. The fragment of the first subunit and the fragment of the second subunit are capable of interacting to form a dimer. In certain embodiments, the first fragment of the first subunit includes an amino acid sequence as shown in SEQ ID NO.: 1. In certain embodiments, the first fragment of the second subunit includes an amino acid sequence as shown in SEQ ID NO.: 2 or SEQ ID NO. 4. In certain embodiments, the first fragment of the first subunit includes an amino acid sequence including SEQ ID NO.: 1 and the first fragment of the second subunit includes an amino acid sequence including SEQ ID NO.: 2 or SEQ ID NO. 4.

In accordance with certain preferred embodiments, a kit for testing compounds for inhibiting herpes simplex virus is provided. The kit includes at least a first reagent which includes a peptide that is substantially homologous to an eighteen amino acid C-terminal fragment of the catalytic unit of herpes simplex virus DNA polymerase. The reagent also includes a fragment of processivity subunit of herpes simplex virus DNA polymerase, in which the C-terminal fragment comprises a fluorescent label. In certain embodiments, the peptide is selected from peptide including SEQ ID NO.: 1. In certain embodiments, the fragment of processivity unit is selected from fragments including SEQ ID NO.: 2 or SEQ ID NO.:4. In certain embodiments, the peptide is selected from peptides including SEQ ID NO.: 1 and the fragment of processivity unit is selected from fragments including SEQ ID NO.: 2 or SEQ ID NO. 4.

In accordance with certain preferred embodiments, a kit is disclosed. The kit includes a reagent solution for testing compounds which inhibit herpes simplex virus. The reagent solution includes a peptide which includes SEQ ID NO.:1 and a protein fragment which includes SEQ ID NO.:2. The peptide includes a fluorescent label.

The kits disclosed here may further include one or more buffers, salts, solvents, proteins, indicators, dyes, or other suitable components necessary for determining protein interactions. One skilled in the art given the benefit of this disclosure will be able to select other suitable components for incorporating into the kits disclosed here. The kits may be designed such that one or more reagents which are temperature sensitive can be kept at a suitable temperature, e.g. −80° C. That is, one or more components of the kits may be kept at a lower temperature than the other reagents and prior to use such reagent can be warmed to room temperature, or the temperature of the assay as the case may be. Accordingly, the kit may comprise a plurality of reagents, e.g. two, three or more, which are mixed together during or before the assay.

In accordance with certain preferred embodiments, all components of the kits disclosed here may be mixed such that a single solution comprises all necessary components for performing an assay to determine protein interaction inhibitors. That is, no mixture of reagents is required by the user. Typically the user would provide a test compound and mix the test compound with a sample of the kit reagent to determine if the test compound could disrupt protein interactions. In other embodiments, however, the components of the kit are stored in separate containers, e.g. vials. Thus, prior to performing assays to identify protein inhibitors, suitable amounts of each component can be added to the test mixture. One skilled in the art given the benefit of this disclosure will be able to design kits suitable for identifying test compounds which inhibit protein interactions.

In accordance with certain preferred embodiments, a composition for treating herpes simplex virus comprising a compound of formula I, or a pharmaceutically suitable salt or solvate thereof. Preferably a salt of compound I is used to treat herpes simplex virus, e.g. hydrochloride, chloride, bromide, sodium, and/or potassium salts, etc. Suitable pharmaceutical salts typically depend on the solubility of the salt, bioavailability of the salt, synthetic feasibility of the salt, etc. One skilled in the art given the benefit of this disclosure will be able to select suitable salts of compound I for treating herpes simplex virus.

In accordance with certain preferred embodiments, a composition for treating herpes simplex virus is disclosed. The composition includes a compound of formula II, or pharmaceutically suitable salt or solvate thereof. Preferably a salt of compound of formula II is used to treat herpes simplex virus, e.g. hydrochloride, chloride, bromide, sodium, and/or potassium salts, etc. Suitable pharmaceutical salts typically depend on the solubility of the salt, bioavailability of the salt, synthetic feasibility of the salt, etc. One skilled in the art given the benefit of this disclosure will be able to select suitable salts of compound I for treating herpes simplex virus.

In accordance with certain preferred embodiments, the compounds disclosed here may be placed into a suitable carrier. That is, compounds I–II typically can be mixed with a carrier, e.g. powders, gelatin, etc., such that suitable forms, e.g. pills, capsules, tablets, etc. can be provided. For example, in preparing a formulation suitable for administration to a mammal, e.g. a human, bovine, etc., a suitable amount of compound I is typically combined with an excipient, diluted by an excipient or enclosed within a carrier that can be in the form of a capsule, sachet, or other container. When the excipient serves as a diluent, it can be a solid, semi-solid, or liquid material that acts as a vehicle, carrier or medium for the active ingredient. Thus, the compositions can be in the form of tablets, pills, powders, lozenges, sachets, cachets, elixirs, suspensions, emulsions, solutions, syrups, creams, aerosols (as a solid or in a liquid medium), ointments, soft and hard gelatin capsules, suppositories, sterile injectable solutions and sterile packaged powders. Examples of suitable carriers, excipients and diluents include but are not limited to lactose, dextrose, sucrose, sorbitol, mannitol, starches, gum acacia, calcium phosphate, alginates, carageenans, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; flavoring agents; and dyes or other coloring agents. The compositions of the present invention can be formulated so they provide quick, sustained or delayed release of the active ingredient after administration to the mammal by procedures which will be readily apparent to those skilled in the art given the benefit of this disclosure. Depending on the intended use , e.g. veterinary uses, human treatment uses, etc., the nature and properties of the carrier may vary, and one skilled in the art given the benefit of this disclosure will be able to select suitable carriers for administration to mammals.

In accordance with certain preferred embodiments, a method of treating herpes simplex virus in a mammal, e.g. a human, comprising administering a pharmaceutically effective amount, e.g. an efficacious amount, of a compound of formula I or formula II, or pharmaceutically suitable salt or solvate thereof, to the mammal is provided. The pharmaceutically effective amount typically depends on the nature of the compound used, e.g. nature of the salt, and preferably comprises an amount suitable to inhibit the herpes simplex virus DNA polymerase. Preferably, the compound is administered to a patient inflicted with herpes simplex virus by oral administration, topical administration, intravenous administration, peritoneal administration, and the like. In embodiments, where the compound is administered orally, preferably the amount administered is between 0.001–20 mg/kg of body weight, more preferably 0.01–15 mg/kg of body weight and most preferably between 0.10–10 mg/kg of body weight. One skilled in the art given the benefit of this disclosure will be able to select suitable amounts for administering to a mammal inflicted with herpes simplex virus. Preferably, the compound is mixed with a suitable carrier, as discussed above, before administration to a mammal. Suitable carriers will be readily apparent to those skilled in the art given the benefit of this disclosure.

It will be recognized by those skilled in the art given the benefit of this disclosure, that certain preferred embodiments of the present invention provide for high-throughput testing of potential inhibitors of protein interactions. The robust methods and kits disclosed here can be employed to test large libraries of compounds in a rapid and cost-effective manner. For example, the methods disclosed here can be used to design arrays comprising the components of the kit such that a plurality of test compounds can be tested in a rapid manner to identify potential test compounds which inhibit or disrupt protein interactions.

The following patent applications and/or patents are incorporated herein by reference in their entireties for all purposes: Coen D M, Digard P E "Inhibitors of Herpes Simplex Virus Replication," U.S. Ser. No. 482,34, filed Feb. 21, 1990, issued as U.S. Pat. No. 5,223,391 Jun. 29, 1993, which mentions screening assays, and also case number unknown (Coen D M, Hogle J M, Elkin C, Zuccola H J, Bridges K G, Lokey, "A Structure-Based Approach to Design Inhibitors of Protein-Processivity Factor Interactions," PCT filed May 12, 2000 for additional background information.

An example of the novel technology is disclosed below. The example is not intended to limit this novel technology in any manner.

EXAMPLE 1

Screening of a Library of Compounds Against Herpes Simplex Virus DNA Polynerase Fragments Peptide probe and MBP-UL42. A peptide comprising the 18 C-terminal amino acids of HSV Pol (peptide E) was synthesized, N-terminally labeled with the pentafluorofluorescein-derivative Oregon Green 514 (Molecular Probes) and HPLC-purified. A truncated version of UL42 (UL42Δ340) was expressed in BL21(de3)pLysS E.coli as maltose binding protein fusion as described [Bridges et al. 2001] and purified over an amylose column (New England Biolabs). UL42Δ340 was shown to retain all known biochemical activities of UL42 [Hamatake et al. 1993; Digard et al. 1993; Tenney et al. 1993]. After elution with 10 mM maltose in 50 mM TrisHCl, 1 mM DTT, 0.5 mM EDTA, 4% Glycerol, 200 mM NaCl and Complete™ protease inhibitors (Roche Molecular Biochemicals), the protein was concentrated when necessary and stored at −80° C. until further use. After thawing, the purification buffer was exchanged to low fluorescent grade reagents (PanVera) and maltose was removed simultaneously using 10-DG Bio-Gel columns (BioRad).

Fluorescence polarization assays. 1 nM of Oregon Green-peptide E was added to 7 uM MBP-UL42Δ340 and kept on ice until the mix was distributed into black 384-well plates (LJL Biosystems) in a total volume of 20 ul per well. The buffer conditions were 50 mM TrisHCl pH 7.5, 1 mM DTT, 0.5 mM EDTA, 150 mM NaCl, 4% Glycerol and 100 ug ml$^{-1}$ bovine gamma globulin. All chemicals were low fluorescent grade (PanVera).

Using this assay, the 16,320 compound Chembridge library that had been purchased by the Harvard Institute of Chemistry and Cell Biology (ICBB) was screened. Small molecules (5 mg ml$^{-1}$ in DMSO; ChemBridge) were screened using 384-pin arrays (Genetix), and 40 nl of each compound was transferred into every well. After incubation between 5 and 45 minutes at room temperature, the FP values were determined in the Analyst plate reader (LJL Biosystems). Chemicals for further testing were obtained from ChemBridge.

DNA polymerase long-chain synthesis assay. Compounds which elicited a decrease in the fluorescence polarization, when compared to control values, were tested for the ability to inhibit long-chain DNA synthesis via inhibition of polymerase subunit assembly [Digard et al. 1995; Bridges et al. 2001] using a poly-A template (Amersham Pharmacia) and an oligo-dT primer (Roche Molecular Biochemicals) on which Pol alone adds only a few bases. Reaction mixtures (50 mM Tris-HCl pH 7.5, 100 mM ammonium sulfate, 3 mM MgCl$_2$, 0.1 mM EDTA, 1 mM DTT, 4% Glycerol, 40 ug ml$^{-1}$ BSA, 100 ug ml$^{-1}$ primer/template, 50 uM α-$^{32}$P-TTP (111 TBq/mmol; NEN Life Science products)), contained 200 fmol of HSV Pol ([Weisshart et al. 1994]), 400 fmol of HSV MBP-UL42 and varying amounts of compound in a final volume of 25 ul. Reactions were carried out at 37° C. for 5 minutes and stopped by adding 5 ul of alkaline loading buffer (2mM EDTA, 50mM NaOH, 2.5% glycerol, 0.025% bromocresol green) and placing them on ice and were then loaded onto an 4% alkaline agarose gel. Gels were dried over night and exposed to phosphorescence screens (BioRad).

Catalytic subunit activity filter binding assay. Compounds which elicited a decrease in fluorescence polarization were tested for the ability to inhibit DNA synthesis by Pol alone using the oligo-(dT)/poly-(dA) primer-template. Reaction mixtures (50 mM TrisHCl pH 7.5, 100 mM ammonium sulfate, 3 mM MgCl$_2$, 0.1 mM EDTA, 1 mM DTT, 4% Glycerol, 40 μg ml$^{-1}$ BSA, 100 μg ml$^{-1}$ primer/template, 50 μM α-$^{32}$P-TTP (111 TBq/mmol)) contained 200 fmol of HSV Pol and various amounts of each compound in a final volume of 25 μl. Reactions were carried out at 37° C. for 25 minutes and stopped by placing 10 μl of the reaction mix onto DE81 filter discs. After washes in sodium hydrogen phosphate, water and ethanol, they were counted in a liquid scintillation analyzer (Packard 1600 TR).

Plaque reduction assay. Confluent monolayers of Vero (African green monkey kidney) cells in 12-well dishes were infected with herpes virus strain 17 dilutions such that each well received between 25 and 50 PFU. Diluted virus was absorbed to cells in 2 ml Dulbecco's modified Eagle's medium containing 2.5% newborn calf serum, 100 U penicillin G ml$^{-1}$ and 100 ug streptomycin sulfate ml$^{-1}$ for 1 hour at 37° C. in a humidified CO$_2$ incubator. After absorption, triplicate infected cultures were overlaid with 2% methyl cellulose in Dulbecco's modified Eagle's medium containing 5% newborn calf serum, 100 U penicillin G ml$^{-1}$, 100 ug streptomycin sulfate ml$^{-1}$ and various concentrations of the compounds which elicited a decrease in fluorescence polarization and incubated at 37° C. in a humidified CO$_2$ incubator. Plaques were visualized by crystal violet staining at 2 to 3 days post infection and were counted on the following day [Coen et al. 1985].

Cytotoxicity assays. Vero cells (5×10$^4$ cells per well) were seeded into 96-well plates and treated with various concentrations of the compounds (which elicited a decrease in the fluorescence polarization) for 72 h in quadruplicates. Cell viability was determined with an XTT (sodium 3'-[1-(phenylaminocarbonyl)-3,4-tetrazolium]-bis (4-methoxy-6-nitro) benzene sulfonic acid hydrate) assay (Roche Molecular Biochemicals) according to the manufacturer's suggestions using a Victor plate reader (Wallac). In parallel, equally compound-treated cells were fixed by adding 95% ethanol, stained with crystal violet solution and washed. After addition of 100 ul acidified ethanol (EtOH:HCl=99:1) to dissolve the crystal violet, the plates were read in the plate reader (Wallac).

Viral yield assay. Vero cells were seeded into 96-well (5×10$^4$ cells per well) tissue culture plates in 0.2 ml Dulbecco's modified Eagle's medium containing 2.5% newborn calf serum and 100 U penicillin G ml$^{-1}$. Cultures were inoculated with HSV strain 17 at an MOI of 5 PFU per cell. The virus inoculum was replaced after two hours with medium containing dilution series of test compounds and left for 24 hours. After two cycles of freeze-thawing, each drug dilution row was transferred to a freshly seeded 96-well plate and serially 1:3 diluted over the whole plate. After two days, plaques were stained and counted under a microscope [Pritchard et al. 1990].

A. Development and validation of a high throughput screen to identify small molecule inhibitors of Pol/UL42 interaction. To demonstrate that the methods provided here are useful in identifying small molecules capable of preventing viral polymerase subunit assembly, a new homogeneous assay using fluorescence polarization (FP) was performed. The Pol portion of the polymerase was present as a fluorescently labeled 18-mer peptide and UL42 as MBP-fusion protein (as described above). Without wishing to be bound by any particular scientific theory, when the Oregon Green-labeled 18mer peptide, corresponding to the last 18 residues of the catalytic subunit is free, it tumbles fast, causing low polarization values. However, upon binding to MBP-UL42, the tumbling rate of the peptide adapts to the rate of the much bulkier binding partner and the polarization increases. The conditions for the assays were as follows: The labeled peptide was kept constant at 1 nM. MBP-UL42Δ340 was used at a concentration range of 1 to 50 μM to determine the $K_d$ value of binding. Hofstee transformation was used to determine the $K_d$ value under the conditions used. A UL42 mutant (UL42I-160) defective for Pol-binding was used to show that the interaction of the peptide with wt UL42 was specific. The weak concentration dependent increase in polarization above 20 μM was mainly due to nonspecific binding (A, blue symbols). The values were used to correct the UL42 wt measurements. To further verify specificity, binding of peptide was competed with 36-mer peptide A derived from the C-terminus of Pol (B). UL42 was held constant at 7 μM.

To determine the $K_d$ value and test binding saturation, we titrated MBP-UL42 into a solution of labeled peptide at constant concentration (FIG. 1A). The resulting $K_d$ value for the interaction of 5 uM is in agreement with constants determined earlier in our laboratory using other methods [Bridges et al. 2001; Bridges et al. 2000]. To further test binding specificity, we competed binding of the labeled peptide to UL42 with unlabeled peptide A, corresponding to the 36 last residues of Pol (FIG. 1B). Both peptides show similar affinity to UL42 [Bridges et al. 2000]. The data indicated that peptide A was able to abrogate binding of the labeled tracer with an $IC_{50}$ of approximately 6 μM using the Hill equation, four parameters, $y=y_0=(axb/cb+xb)$.

B. Screen of 16,320 compounds. 0.6% of all the compounds screened (Table 1), exhibited polarization values outside the ±3 SD-interval that served as selection criterion, indicating a change in the nature of the binding state of the labeled Pol-peptide. 0.4% of these however turned out to be false positives, due to intrinsic fluorescence of the small molecule, adsorption to the well and/or precipitation. 0.2% of the initial hits were reproduced by the FP assay but only a third of these proved to be active in functional assays.

TABLE I

Summary of Screening

| | | |
|---|---|---|
| Compounds Screened | 16,320 | 100% |
| Total Possible Hits | 98 | 0.6% |
| False Positives | 61 | 0.4% |
| Hits to Reproduce | 37 | 0.2% |
| Most potential hits | 9 | 0.06% |

Figure 2:
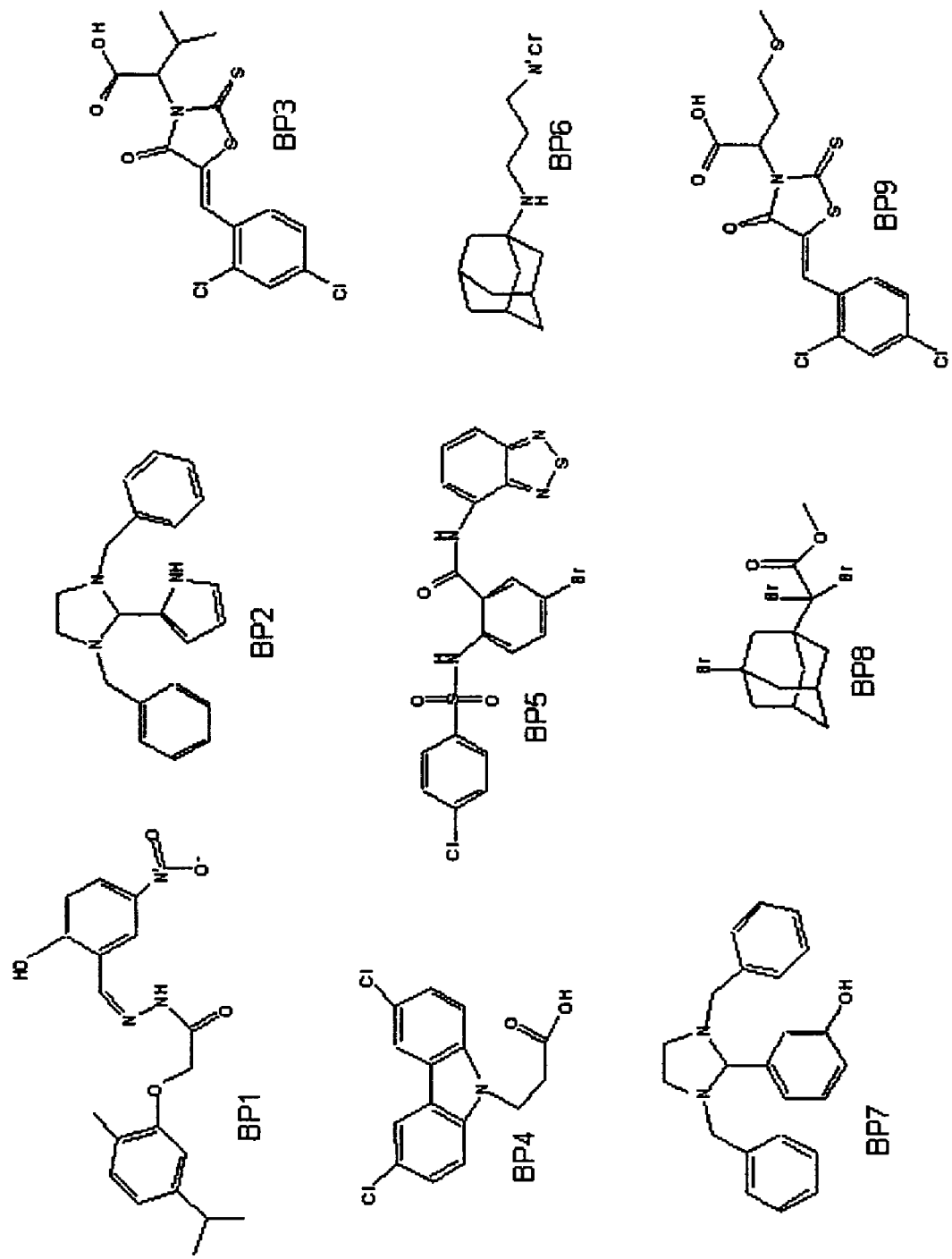
FIG. 2 shows the structures of several compounds identified to inhibit protein interactions, in accordance with certain preferred embodiments.

The structures of the 9 selected, most efficacious compounds (FIG. 2) show similarities among each other and/or with related structures in the pool of the tested molecules; many of those inactive molecules exhibit larger substituents than the selected, active ones. Interestingly, some of the selected small molecules are very similar to molecules independently found that are shown to act as protein/protein-interaction inhibitors [Degterev et al. 2001] which provides further support for the specificity. To ensure the integrity of the actual structure, all the compounds of the library were reordered and subjected to mass spectroscopy analysis (data not shown). Although impurities were detected, the main peak was present for each compound. To ensure comparable data, internal reference values (peptide only, no compound, no DMSO) were included on each screening plate.

Figure 3:
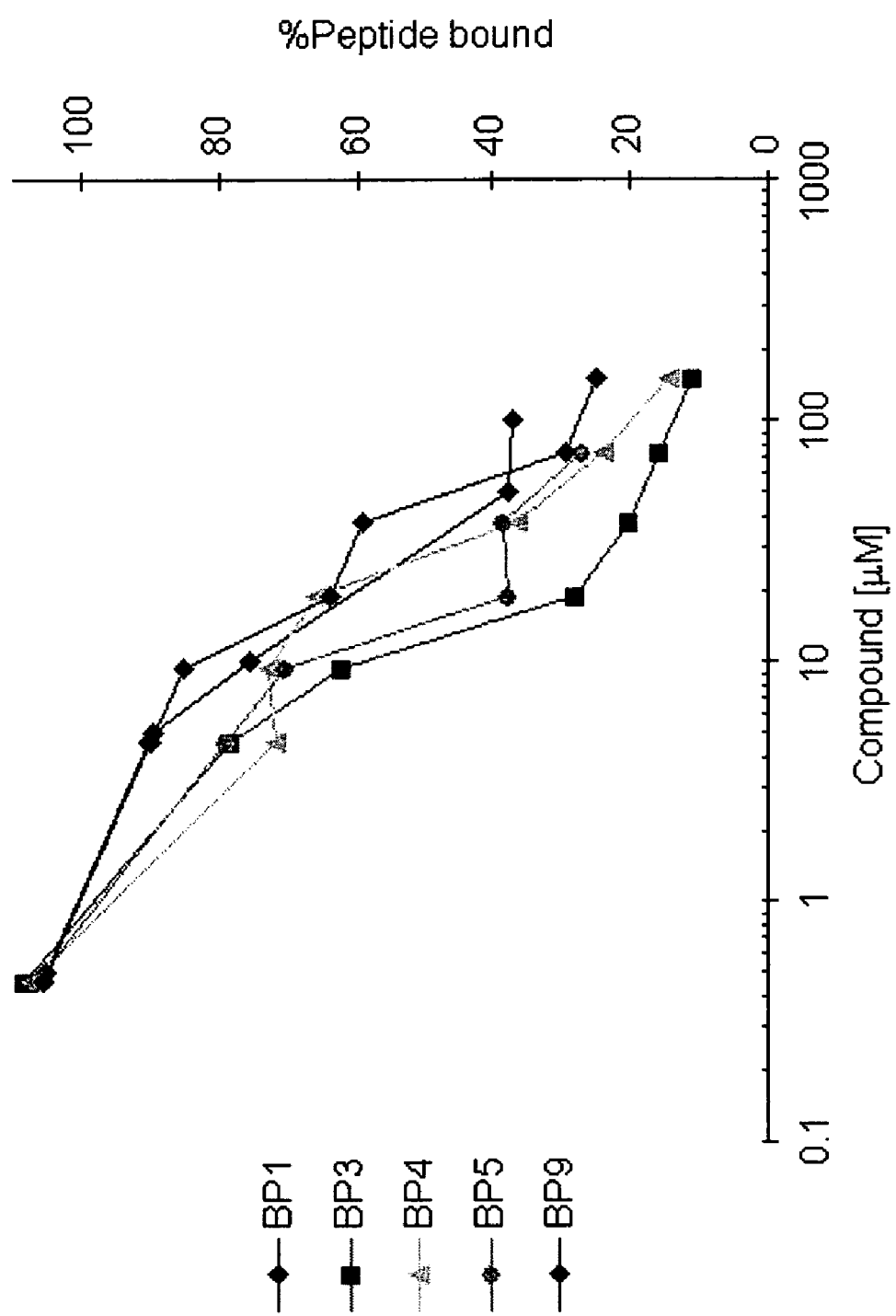
FIG. 3 is a dose dependency curve with respect to fluorescence polarization, in accordance with certain preferred embodiments.

C. FP-Dose dependence of the selected compounds. To test whether the change in the polarization value showed dose dependency (FIG. 3), we serially diluted the test compounds and plotted the resulting values against the free peptide control. The compounds were tested as follows: Selected compounds were serially diluted in 50% DMSO/low fluorescence buffer (final DMSO concentration≦2%) and mixed with 1 nM of peptide/7 μM MBP-UL42Δ340. After 10 minutes incubation, the polarization was measured in the Analyst plate reader (LJL Biosystems). The resulting polarization was plotted against the free peptide control. Background was determined by adding DMSO at the appropriate concentration.

BP1, BP3, BP4, BP5 and BP9 did show a dose dependent change in the FP signal. As the structurally similar compounds behaved comparably in this assay, exhibiting $IC_{50}$ values between 10 and 40 uM,. Therefore, it appears that some of these compounds act in a specific manner.

Figure 4:
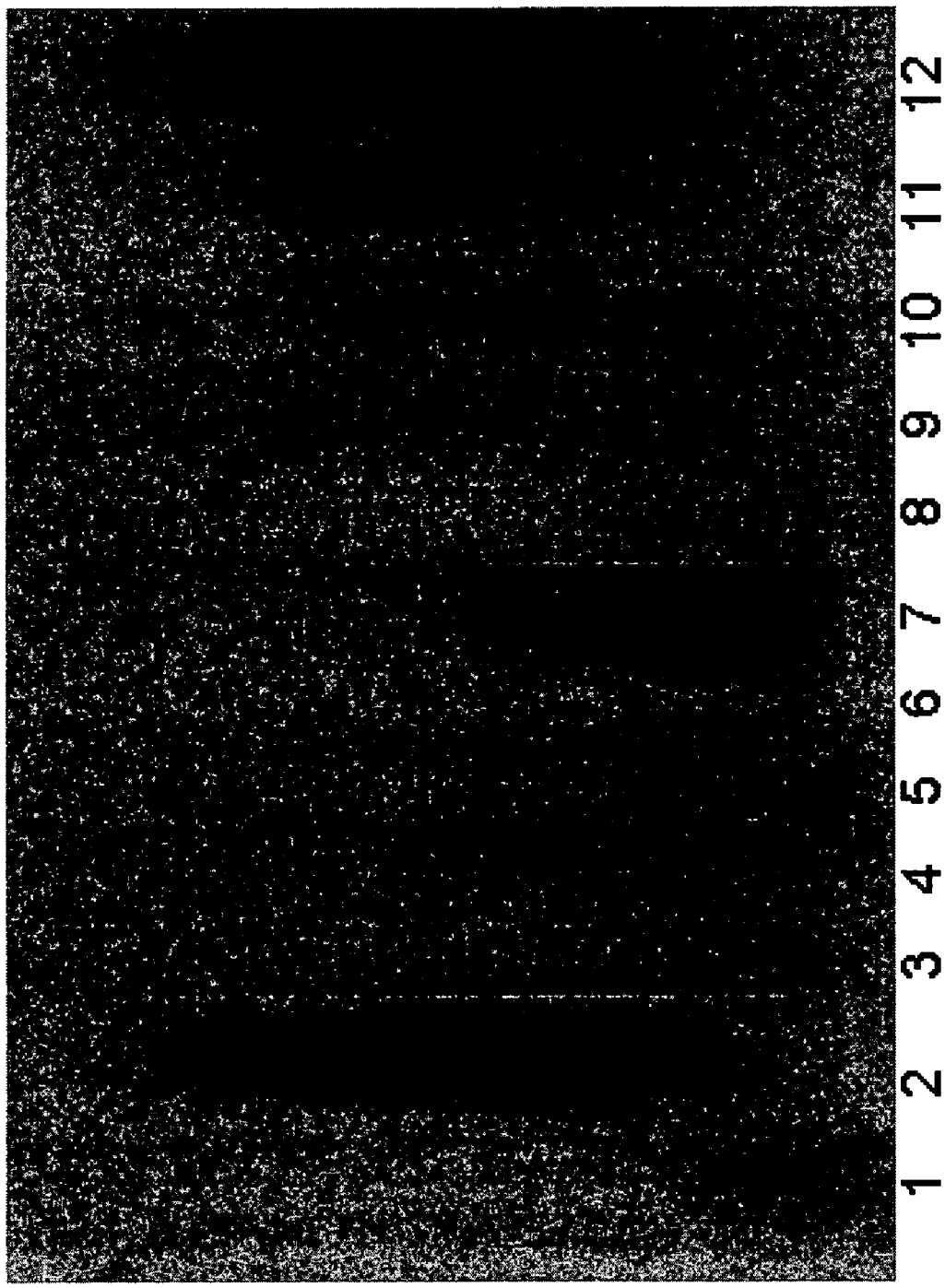
FIG. 4 is a gel showing long chain DNA synthesis inhibition, in accordance with certain preferred embodiments.

D. Pol/UL42 assay. Using a long-chain DNA synthesis assay by DNA polymerase [Digard et al. 1995; Bridges et al. 2001], the compounds shown in FIG. 2 were tested for the ability to interfere with the subunit interaction in presence of the whole catalytic subunit and thus inhibiting the UL42-dependent long-chain DNA synthesis (FIG. 4). The conditions for the gel were as follows:

The selected compounds were tested for the ability to inhibit long-chain DNA synthesis via inhibition of polymerase subunit assembly using a poly-dA template and an oligo-dT primer on which Pol alone adds only a few bases (lane 1). Lane 2: Pol/UL42 as positive control; lane 3: Pol/UL42+40 mM peptide A as known inhibitor and negative control; lane 4: Pol/UL42+20 mM peptide A; lane 5: Pol/UL42+BP1; lane 6: Pol/UL42+BP3; lane 7: Pol/UL42±BP5. Concentration of compounds was 30 μM. Lane 8–12: Pol/UL42BP9 at 100, 75, 50, 25 and 12 μM. Reaction mixtures (50 mM TrisHCl pH 7.5, 100 mM ammonium sulfate, 3 mM MgCl2, 0.1 mM EDTA, 1 mM DTT, 4% Glycerol, 40 μg ml$^{-1}$ BSA, 100 μg ml$^{-1}$ primer/template, 50 μM 32P-TTP), contained 200 fmol of HSV Pol, 400 fmol of HSV UL42 and indicated amounts of each compound in a final volume of 25 μl. Reactions were carried out at 37° C. for 5 minutes and stopped by adding 5 μl of alkaline loading buffer and placing them on ice. They were then loaded onto an 4% alkaline agarose gel. Gels were dried over night and exposed to phosphorescence screens.

Referring to FIG. 4, BP1 (lane 5), BP3 (lane 6), BP5 (lane 7) and BP9 (lanes 8–12) greatly reduced the ability of UL42 to stimulate long-chain synthesis by Pol and allowed only formation of smaller products, in agreement with the dose dependent FP assay (see above). Again, the structurally related molecules BP3 and BP9 yielded similar effects. The other two compounds, BP1 and BP5, which show an effect in this experiment, exhibit both peptide-like features in their structure, thus enabling specific interactions with one of the subunits. As a control for the quantification via phosphor imager, the samples were also loaded onto DE-81 filters and analyzed in a scintillation counter. The results of the two methods were similar (data not shown).

Figure 5:
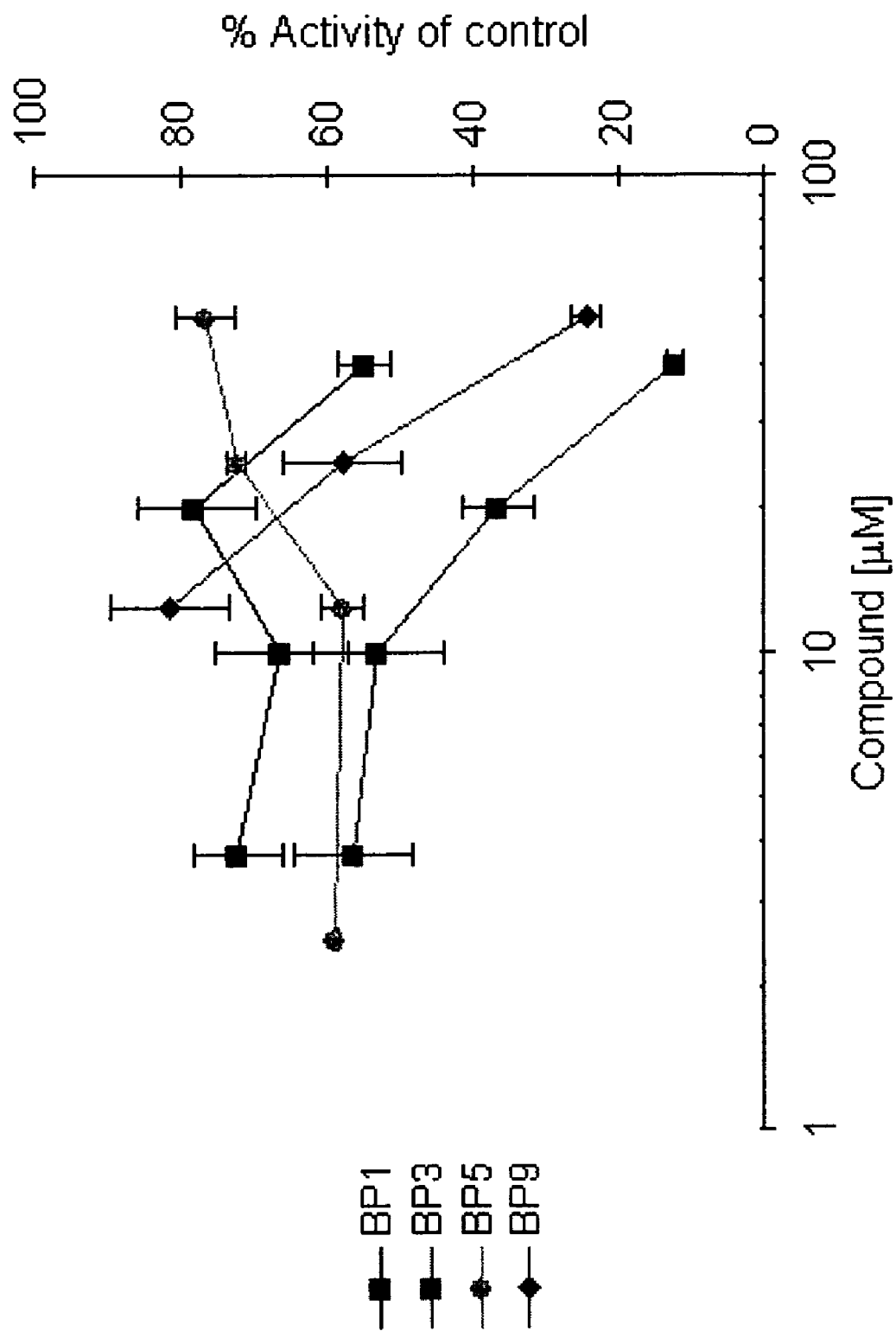
FIG. 5 is a graph showing the effect of certain compounds on the activity of a fragment, in accordance with certain preferred embodiments.

E. Pol alone assay (Selectivity of identified small molecule inhibitors). In order to determine whether the inhibition of the long-chain DNA synthesis was in fact due to prevention of subunit interaction, DNA synthesis by Pol in absence of UL42 was tested using a filter binding assay. The amount of incorporated radioactive nucleotide was monitored at increasing concentration of the respective test compound (FIG. 5). In the presence of the structurally related BP3 and BP9, Pol activity was significantly reduced at higher concentrations. BP1 and BP5, both of which share peptide-like features, did not show a significant change in Pol activity in presence of higher compound concentration, inhibiting the Pol/UL42 complex more potently than Pol alone, suggesting a different mode of action than BP3 and BP9. Aliquots of the reaction mix were also ran out on a sequencing gel (data not shown) showing a decreased amount of product formation in the case of BP3.

Table 2 summarizes the $IC_{50}$ values of BP1, BP3, BP5 and BP9 as determined by FP analysis, long-chain DNA synthesis assay and filter binding assay for Pol activity in absence of UL42. For BP3 and BP9 all these values lay within the same range of magnitude, indicating long-chain DNA synthesis inhibition being caused by interference with Pol activity alone. For BP1 and BP5 the $IC_{50}$ values for Pol activity alone are significantly higher than the other results, indicating a more specific mechanism of action different from the other two compounds.

TABLE 2

$IC_{50}$ values of selected compounds

| Compound | $IC_{50}$ (uM) for Pol/UL42 interaction by FP | $IC_{50}$ (uM) for Pol alone activity | $IC_{50}$ (uM) for Pol/UL42 long-chain DNA synthesis |
| --- | --- | --- | --- |
| BP1 | 35 | >100 | 25 |
| BP3 | 12 | 25 | 30 |
| BP5 | 15 | >100 | 26 |
| BP9 | 48 | 25 | 25 |

The DNA synthesis inhibition was performed as follows:

The compounds were tested for the ability to inhibit DNA synthesis by Pol alone using a poly-dA template and an oligo-dT primer Reaction mixtures (50 mM TrisHCl pH 7.5, 100 mM ammonium sulfate, 3 mM $MgCl_2$, 0.1 mM EDTA, 1 mM DTT, 4% Glycerol, 40 μg ml$^{-1}$ BSA, 100 μg ml$^{-1}$ primer/template, 50 μM $^{32}$P-TTP), contained 200 fmol of HSV Pol and indicated amounts of each compound in a final volume of 25 μl. Reactions were carried out at 37° C. for 25 minutes and stopped by placing 10 μl of the reaction mix onto DE81 filter discs. After washes in sodium hydrogen phosphate, water and ethanol, they were counted in a liquid scintillation counter.

E. Antiviral assay. With two of the inhibitors showing specific effects in in vitro functional assays, experiments to test the influence of the compounds on herpes virus growth were performed. Monolayers of Vero cells in Dulbecco's modified Eagle's medium containing 2.5% newborn calf serum, 100 U penicillin G ml$^{-1}$ and 100 μg streptomycin sulfate ml$^{-1}$ in 96-well dishes were infected with an MOI of 5. After absorption, selected compounds were added to duplicate wells and serially diluted to concentrations indicated in the figure and incubated at 37° C. in a humidified $CO_2$ incubator for 24 h. Culture lysates were serially diluted in a separate set of uninfected cultures. After 2 d incubation, plaques were counted and virus titers calculated.

Figure 6:
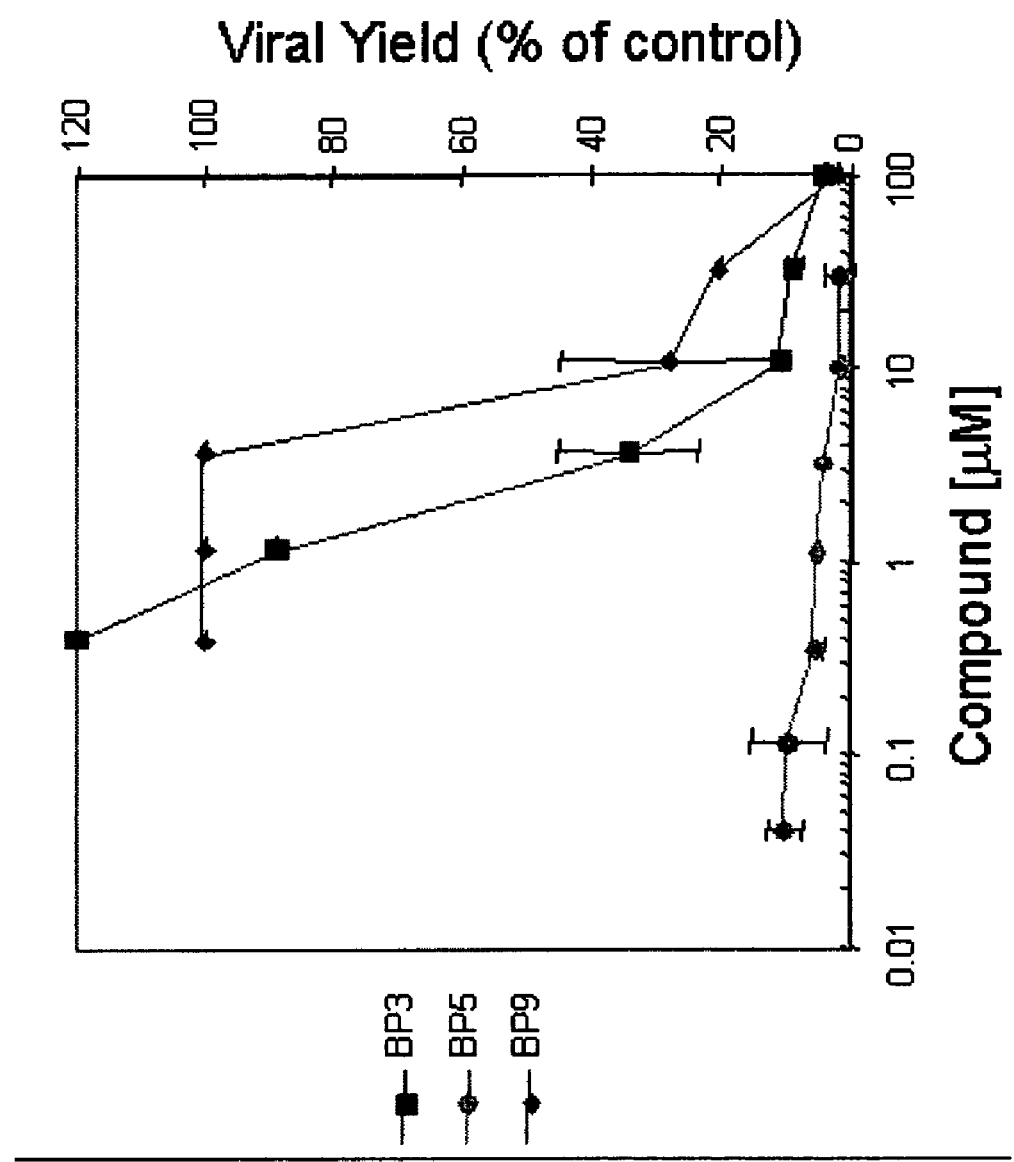
FIG. 6 is a graph of percent viral yield as a function of compound concentration, in accordance with certain preferred embodiments.
Figure 7:
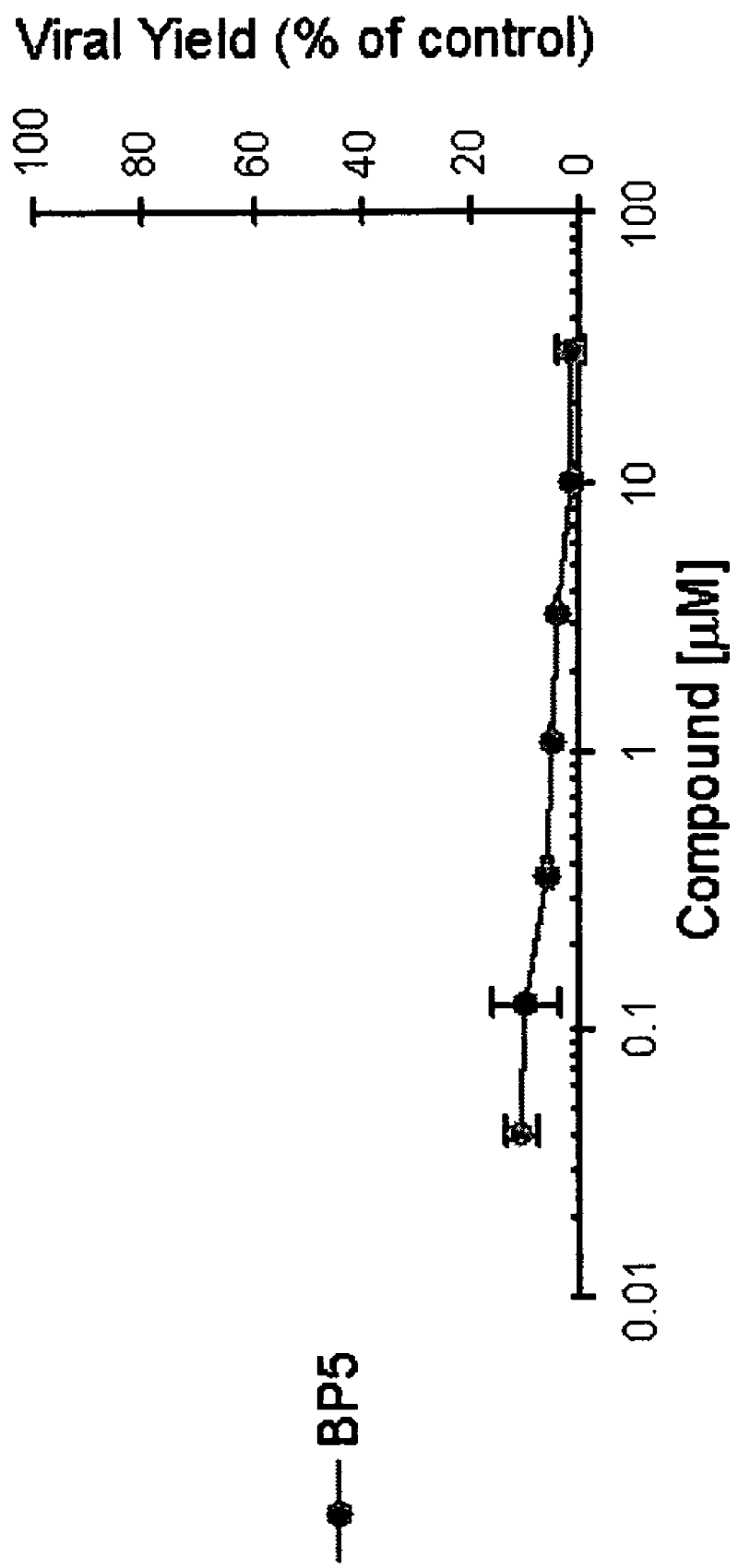
FIG. 7 is a graph of viral yield as a function of BP5 concentration, in accordance with certain preferred embodiments.

First, the 50% toxic dose of the compounds for the Vero cell line used in the viral yield reduction experiment (Table 3) was measured. BP5 exhibited a 50% toxic dose of 50 uM; determination of toxicity for BP1 was hampered by solubility problems in the culture medium used, but resulted in values similar to BP5 (see FIG. 6). In the viral yield reduction assay [Pritchard et al. 1990] BP5 showed an $ED_{90}$ value of 400 nM (see FIG. 7). Although the 50% toxic dose of BP5 lies at 50 uM, its potential therapeutic range is still considerable. In parallel, plaque reduction assays (data not shown) were performed, supporting the findings of the viral yield reduction assay. BP5 was able to completely abolish plaque formation.

TABLE 3

Toxicity of Selected Compounds

| Toxicity | $IC_{50}$ (uM) |
| --- | --- |
| BP1 | 20 |
| BP3 | 200 |
| BP5 | 50 |
| BP9 | 200 |

TABLE 4

SEQUENCE LISTINGS

SEQ ID NO.: 1
Ac-ATAEETRRMLHRAFDTLA-NH$_2$

SEQ ID NO.:2
MTDSPGGVAPASPVEDASDASLGQPEEGAPCQVVLQGAELNGILQAFAPL

RTSLLDSLLVMGDRGILIHNTIFGEQVFLPLEHSQFSRYRWRGPTAAFLS

LVDQKRSLLSVFRANQYPDLRRVELAITGQAPFRTLVQRIWTTTSDGEAV

ELASETLMKRELTSFVVLVPQGTPDVQLRLTRPQLTKVLNATGADSATPT

TFELGVNGKFSVFTTSTCVTFAAREEGVSSSTSTQVQILSNALTKAGQAA

ANAKTVYGENTHRTFSVVVDDCSMRAVLRRLQVGGGTLKFFLTTPVPSLC

VTATGPNAVSAVFLLKLPQKICLDWLGHSQGSPSAGSSAS

SEQ ID NO.:3
MFSGGGGPLSPGGKSAARAASGFFAPAGPRGASRGPPPCLRQNFYKPYLA

PVGTQQKPTGPTQRHTYYSECDEFRFIAPRVLDEDAPPEKRAGVHDGHLK

RAPKVYCGGDERDVLRVGSGGFWPRRSRLWGGVDHAPAGFNPTVTVFHVY

DILENVEHAYGMRAAQFHARFMDAITPTGTVITLLGLTPEGHRVAVHVYG

TRQYFYMNKEEVDRHLQCRAPRDLCERMAAALRESPGASFRGISADHFEA

EVVERTDVYYYETRPALFYRVYVRSGRVLSYLCDNFCPAIKKYEGGVDAT

TRFILDNPGFVTFGWYRLKPGRNNTLAQPAAPMAFGTSSDVEFNCTADNL

AIEGGMSDLPAYKLMCFDIECKAGGEDELAFPVAGHPEDLVIQISCLLYD

LSTTALEHVLLFSLGSCDLPESHLNELAARGLPTPVVLEFDSEFEMLLAF

MTLVKQYGPEFVTGYNIINFDWPFLLAKLTDIYKVPLDGYGRMNGRGVFR

VWDIGQSHFQKRSKIKVNGMVNIDMYGIITDKIKLSSYKLNAVAEAVLKD

KKKDLSYRDIPAYYAAGPAQRGVIGEYCIQDSLLVGQLFFKFLPHLELSA

VARLAGINITRTIYDGQQIRVFTCLLRLADQKGFILPDTQGRFRGAGGEA

TABLE 4-continued

SEQUENCE LISTINGS

PKRPAAAREDEERPEEEGEDEDEREEGGGEREPEGARETAGRHVGYQGAR

VLDPTSGFHVNPVVVFDFASLYPSIIQAHNLCFSTLSLRADAVAHLEAGK

DYLEIEVGGRRLFFVKAHVRESLLSILLRDWLAMRKQIRSRIPQSSPEEA

VLLDKQQAAIKVVCNSVYGFTGVQHGLLPCLHVAATVTTIGREMLLATRE

YVHARWAAFEQLLADFPEAADMRAPGPYSMRIIYGDTDSIFVLCRGLTAA

GLTAVGDKMASHISRALFLPPIKLECEKTFTKLLLIAKKKYIGVIYGGKM

LIKGVDLVRKNNCAFINRTSRALVDLLFYDDTVSGAAAALAERPAEEWLA

RPLPEGLQAFGAVLVDAHRRITDPERDIQDFVLTAELSRHPRAYTNKRLA

HLTVYYKLMARRAQVPSIKDRIPYVIVAQTREVEETVARLAALRELDAAA

PGDEPAPPAALPSPAKRPRETPSPADPPGGASKPRKLLVSELAEDPAYAI

AHGVALNTDYYFSHLLGAACVTFKALFGNNAKITESLLKRFIPEVWHPPD

DVAARLRTAGFGAVGAGATAEETRRMLHRAFDTLA

SEQ ID NO.:4
MTDSPGGVAPASPVEDASDASLGQPEEGAPCQVVLQGAELNGILQAFAPL

RTSLLDSLLVMGDRGILIHNTIFGEQVFLPLEHSQFSRYRWRGPTAAFLS

LVDQKRSLLSVFRANQYPDLRRVELAITGQAPFRTLVQRIWTTTSDGEAV

ELASETLMKRELTSFVVLVPQGTPDVQLRLTRPQLTKVLNATGADSATPT

TFELGVNGKFSVFTTSTCVTFAAREEGVSSSTSTQVQILSNALTKAGQAA

ANAKTVYGENTHRTFSVVVDDCSMRAVLRRLQVGGGTLKFFLTTPVPSLC

VTATGPNAVSAVFLLKPQKICLDWLGHSQGSPSAGSSASRASGSEPTDSQ

DSASDAVSHGDPEDLDGAARAGEAGALHACPMPSSTTRVTPTTKRGRSGG

EDARADTALKKPKTGSPTAPPPADPVPLDTEDDSDAADGTAARPAAPDAR

SGSRYACYFRDLPTGEASPGAFSAFRGGPQTPYGFGFP

The following citations are incorporated herein by reference in their entireties for all purposes:

Gottlieb, J. Marcy, A. I., Coen, D. M. and Chaliberg, M. D. (1990). "The herpes simplex virus type 1 UL42 gene product; a subunit of DNA polymerase that functions to increase processivity. J. Virol. 64, 5976–5987;

Gottlieb J, Challberg M D. (1994) Interaction of herpes simplex virus type 1 DNA polymerase and the UL42 accessory protein with a model primer template. J Virol., Aug; 68(8):4937–45;

Weisshart, K., Chow, C. S. and Coen, D. M. (1999) "Herpes simplex virus processivity factor UL42 imparts increased DNA-binding specificity to the viral DNA polymerase and decreased dissociation from primer-template without reducing the elongation rate." J. Virol. 73, 55–66;

Marsden, H. S., Murphy M., McVery, G. L., MacEachren, K. A. Owsianka, A. M. and Stow, N. D. (1994) "Role of the carboxy terminus of herpes simplex virus type 1 DNA polymerase in its interaction with UL42." J. Gen. Virol., 75, 3127–3135;

Digard, P., Chow, C. S. Pirrit, L. and Coen D M. (1993) Functional analysis of herpes simplex virus UL42 protein. J. Virol. 67, 1159–1168;

Digard, P., Bebrin, W. R., Weisshart, K. and Coen, D. M. (1993) The extreme C terminus of herpes simplex virus DNA polymerase is crucial for functional interaction with processivity factor UL42 and for viral replication. J. Virol. 67, 398–406;

Tenney, D. J., Huriburt, W. W., Bifano, M., Stevens, J. T., Michelleti, P. A., Hamatake, R. K. and Cordingley, M. G. (1993) Deletions of the carboxy terminus of herpes simplex virus type 1 UL42 define a conserved amino-terminal functional domain. J. Virol. 67, 1959–1966;

Tenney, D. J., Michelleti, P. A., Stevens, J. T., Hamatake, R. K., Mathews, J. T., Sanchez, A. R., Huriburt, W. W. Bifano, M. and Cordingley, M. G. (1993) Mutations in the C terminus of herpes simplex virus type 1 DNA polymerase can affect bonding and stimulation by its accessory protein UL42 without affecting basal polymerase activity. J. Virol. 67, 543–547;

Stow N D, Hammarsten O, Arbuckle M I, Elias P. (1993) Inhibition of herpes simplex virus type 1 DNA replication by mutant forms of the origin-binding protein. Virology. Oct; 196(2):413–8;

Digard, P., Coen, D. M. (1990) A novel functional domain of an alpha-like DNA polymerase. The binding site on the herpes simplex virus polymerase for the viral UL42 protein. J Biol Chem. October 15;265(29):17393–6;

Zuccola H J, Filman D J, Coen D M, Hogle J M.(2000) The crystal structure of an unusual processivity factor, herpes simplex virus UL42, bound to the C terminus of its cognate polymerase. Mol Cell. Feb;5(2):267–78;

Chow C S, Coen D M. (1995) Mutations that specifically impair the DNA binding activity of the herpes simplex virus protein UL42. J Virol., Nov;69(11):6965–71.

Digard P, Williams K P, Hensley P, Brooks I S, Dahl C E, Coen D M. (1995) Specific inhibition of herpes simplex virus DNA polymerase by helical peptides corresponding to the subunit interface. Proc Natl Acad Sci USA., February 28;92(5):1456–60;

Digard P, Bebrin W R, Coen D M. (1995) Mutational analysis of DNA polymerase substrate recognition and subunit interactions using herpes simplex virus as prototype. Methods Enzymol.;262:303–22;

Loregian A, Papini E, Satin B, Marsden H S, Hirst T R, Palu G. (1999) Intranuclear delivery of an antiviral peptide mediated by the B subunit of *Escherichia coli* heat-labile enterotoxin. Proc Natl Acad Sci USA., April 27;96(9): 5221–6;

Hamatake R K, Bifano M, Tenney D J, Hurlbut W W, Cordingley M G. (1993) The herpes simplex virus type 1 DNA polymerase accessory protein, UL42, contains a functional protease-resistant domain. J Gen Virol. Oct;74 ( Pt 10):2181–9;

Weisshart K, Kuo A A, Hwang C B, Kumura K, Coen D M. (1994) Structural and functional organization of herpes simplex virus DNA polymerase investigated by limited proteolysis. J Biol Chem., September 9;269(36):22788–96;

Coen D M, Fleming H E Jr, Leslie L K, Retondo M J. (1985) Sensitivity of arabinosyladenine-resistant mutants of herpes simplex virus to other antiviral drugs and mapping of drug hypersensitivity mutations to the DNA polymerase locus. J Virol., Feb53(2):477–88;

Pritchard C G, Stefano J E. (1990) Amplified detection of viral nucleic acid at subattomole levels using Q beta replicase. Ann Biol Clin (Paris).,48(7):492–7;

Bridges K G, Chow C S, Coen D M. (2001) Identification of crucial hydrogen-bonding residues for the interaction of herpes simplex virus DNA polymerase subunits via peptide display, mutational, and calorimetric approaches. J Virol., Jun;75(11):4990–8;

Bridges K G, Hua Q, Brigham-Burke M R, Martin J D, Hensley P, Dahl C E, Digard P, Weiss M A, Coen D M. (2000) Secondary structure and structure-activity relationships of peptides corresponding to the subunit interface of herpes simplex virus DNA polymerase. J Biol Chem., January 7;275(1):472–8; and Degterev A, Lugovskoy A, Cardone M, Mulley B, Wagner G, Mitchison T, Yuan J. (2001) Identification of small-molecule inhibitors of interaction between the BH3 domain and Bcl-xL. Nat Cell Biol., Feb;3(2):173–82.

Although the invention has been described in terms of certain preferred embodiments, one skilled in the art given the benefit of this disclosure will recognize that other substitutions, modifications and alterations are possible. The following claims are intended to cover such substitutions, modification and alterations.

What is claimed is:

1. A method for determining inhibitors of subunit interaction comprising:

providing a test sample comprising at least a first viral polymerase subunit or fragment thereof and at least a second viral polymerase subunit or fragment thereof, the first subunit or fragment thereof and the second subunit or fragment thereof which interacts together and the first or second subunit or fragment thereof comprising a fluorescent label;

measuring fluorescence polarization of the test sample;

combining at least one test compound and the test sample to form a test mixture;

measuring fluorescence polarization of the test mixture; and comparing fluorescence polarization of the test mixture with fluorescence polarization of the test sample to determine if the at least one test compound has inhibits subunit interaction.

2. The method of claim 1 in which the first viral polymerase subunit or fragment thereof includes a peptide having SEQ ID No.: 1.

3. The method of claim 1 in which the second viral polymerase subunit or fragment thereof includes a peptide having SEQ ID No.:2.

4. The method of claim 1 wherein the at least one test compound includes a plurality of test compounds.

5. The method of claim 1 in which the fluorescent label comprises pentafluorescein-derivative Oregon Green 514.

6. The method of claim 1 in which the at least one test compound is a member of a combinatorial library.

7. The method of claim 6 in which remaining members of the library are sequentially tested in a plurality of test mixtures.

8. A method of testing compounds for inhibiting herpes simplex virus DNA polymerase, the method comprising:

providing a test sample comprising a peptide which is substantially homologous to an eighteen amino acid C-terminal fragment of catalytic unit of herpes simplex virus DNA polymerase and a functional fragment of processivity subunit of herpes simplex virus DNA polymerase, the C-terminal fragment of catalytic unit of herpes simplex virus DNA polymerase comprising a fluorescent label;

measuring fluorescence polarization of the test sample;

combining at least one test compound and test sample to form a test mixture; and measuring fluorescence polarization of the test mixture; and comparing fluorescence polarization of the test mixture to fluorescence polarization of the test sample to determine level of inhibition of the herpes simplex virus DNA polymerase by the test compound.

9. The method of claim 8 in which a decrease in fluorescence polarization of test mixture, when compared to fluorescence polarization of test sample, can be correlated to a decrease in DNA synthesis by herpes simplex virus DNA polymerase.

10. The method of claim 9 in which the C-terminal fragment comprises a peptide including SEQ ID NO.:1.

11. The method of claim 9 in which the functional fragment of the processivity subunit comprises a protein including SEQ ID NO.: 2.

12. The method of claim 9 in which the C-terminal fragment comprises a peptide including SEQ ID NO.:1 and the functional fragment of the processivity subunit comprising a protein including SEQ ID NO.: 2.

13. The method of claim 1, wherein the test compound comprises the formula

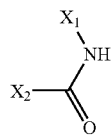

or pharmaceutically suitable salt or solvate thereof, wherein $X_1$ is

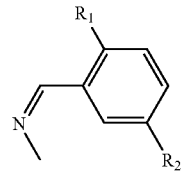

and $X_2$ is

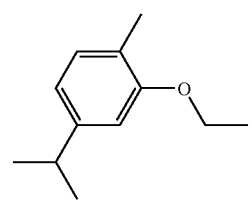

wherein each of $R_1$ and $R_2$ is a member selected from the group consisting of: —$NO_2$, —$NH_2$, —OH, —COOH, —Cl, —Br, —I, and —O—X, wherein X is a saturated or unsaturated hydrocarbon including 1–8 carbon atoms.

14. The method of claim 1, wherein the test compound comprises the formula

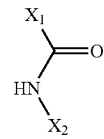

or a pharmaceutically suitable salt or solvate thereof, wherein $X_1$ is

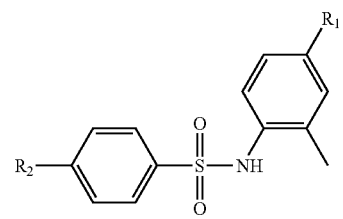

and $X_2$ is

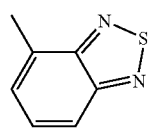

wherein each of $R_1$ and $R_2$ is a member selected from the group consisting of: —$NO_2$, —$NH_2$, —OH, —COOH, —Cl, —Br, —I, and —O—X, wherein X is a saturated or unsaturated hydrocarbon including 1–8 carbon atoms.

* * * * *

SEQUENCE LISTING

```
<160> NUMBER OF SEQ ID NOS: 4

<210> SEQ ID NO 1
<211> LENGTH: 18
<212> TYPE: PRT
<213> ORGANISM: herpes simplex virus
<220> FEATURE:
<221> NAME/KEY: MISC_FEATURE
<222> LOCATION: (1)..(1)
<223> OTHER INFORMATION: acetylated amino acid
<220> FEATURE:
<221> NAME/KEY: MISC_FEATURE
<222> LOCATION: (18)..(18)
<223> OTHER INFORMATION: amidated amino acid

<400> SEQUENCE: 1

Ala Thr Ala Glu Glu Thr Arg Arg Met Leu His Arg Ala Phe Asp Thr
1               5                   10                  15

Leu Ala

<210> SEQ ID NO 2
<211> LENGTH: 339
<212> TYPE: PRT
<213> ORGANISM: herpes simplex virus

<400> SEQUENCE: 2

Met Thr Asp Ser Pro Gly Gly Val Ala Pro Ala Ser Pro Val Glu Asp
1               5                   10                  15

Ala Ser Asp Ala Ser Leu Gly Gln Pro Glu Glu Gly Ala Pro Cys Gln
                20                  25                  30

Val Val Leu Gln Gly Ala Glu Leu Asn Gly Ile Leu Gln Ala Phe Ala
            35                  40                  45

Pro Leu Arg Thr Ser Leu Leu Asp Ser Leu Leu Val Met Gly Asp Arg
        50                  55                  60

Gly Ile Leu Ile His Asn Thr Ile Phe Gly Glu Gln Val Phe Leu Pro
65                  70                  75                  80

Leu Glu His Ser Gln Phe Ser Arg Tyr Arg Trp Arg Gly Pro Thr Ala
                85                  90                  95

Ala Phe Leu Ser Leu Val Asp Gln Lys Arg Ser Leu Leu Ser Val Phe
            100                 105                 110

Arg Ala Asn Gln Tyr Pro Asp Leu Arg Arg Val Glu Leu Ala Ile Thr
        115                 120                 125

Gly Gln Ala Pro Phe Arg Thr Leu Val Gln Arg Ile Trp Thr Thr Thr
    130                 135                 140

Ser Asp Gly Glu Ala Val Glu Leu Ala Ser Glu Thr Leu Met Lys Arg
145                 150                 155                 160

Glu Leu Thr Ser Phe Val Val Leu Val Pro Gln Gly Thr Pro Asp Val
                165                 170                 175

Gln Leu Arg Leu Thr Arg Pro Gln Leu Thr Lys Val Leu Asn Ala Thr
            180                 185                 190
```

-continued

```
Gly Ala Asp Ser Ala Thr Pro Thr Thr Phe Glu Leu Gly Val Asn Gly
            195                 200                 205

Lys Phe Ser Val Phe Thr Thr Ser Thr Cys Val Thr Phe Ala Ala Arg
    210                 215                 220

Glu Glu Gly Val Ser Ser Thr Ser Thr Gln Val Gln Ile Leu Ser
225                 230                 235                 240

Asn Ala Leu Thr Lys Ala Gly Gln Ala Ala Asn Ala Lys Thr Val
                245                 250                 255

Tyr Gly Glu Asn Thr His Arg Thr Phe Ser Val Val Asp Asp Cys
                260                 265                 270

Ser Met Arg Ala Val Leu Arg Leu Gln Val Gly Gly Thr Leu
                275                 280                 285

Lys Phe Leu Thr Thr Pro Val Pro Ser Leu Cys Val Thr Ala Thr
    290                 295                 300

Gly Pro Asn Ala Val Ser Ala Val Phe Leu Leu Lys Pro Gln Lys Ile
305                 310                 315                 320

Cys Leu Asp Trp Leu Gly His Ser Gln Gly Ser Pro Ser Ala Gly Ser
                325                 330                 335

Ser Ala Ser
```

<210> SEQ ID NO 3
<211> LENGTH: 1235
<212> TYPE: PRT
<213> ORGANISM: herpes simplex virus

<400> SEQUENCE: 3

```
Met Phe Ser Gly Gly Gly Gly Pro Leu Ser Pro Gly Gly Lys Ser Ala
1               5                   10                  15

Ala Arg Ala Ala Ser Gly Phe Phe Ala Pro Ala Gly Pro Arg Gly Ala
                20                  25                  30

Ser Arg Gly Pro Pro Pro Cys Leu Arg Gln Asn Phe Tyr Asn Pro Tyr
            35                  40                  45

Leu Ala Pro Val Gly Thr Gln Gln Lys Pro Thr Gly Pro Thr Gln Arg
    50                  55                  60

His Thr Tyr Tyr Ser Glu Cys Asp Glu Phe Arg Phe Ile Ala Pro Arg
65                  70                  75                  80

Val Leu Asp Glu Asp Ala Pro Pro Glu Lys Arg Ala Gly Val His Asp
                85                  90                  95

Gly His Leu Lys Arg Ala Pro Lys Val Tyr Cys Gly Gly Asp Glu Arg
                100                 105                 110

Asp Val Leu Arg Val Gly Ser Gly Gly Phe Trp Pro Arg Arg Ser Arg
            115                 120                 125

Leu Trp Gly Gly Val Asp His Ala Pro Ala Gly Phe Asn Pro Thr Val
    130                 135                 140

Thr Val Phe His Val Tyr Asp Ile Leu Glu Asn Val Glu His Ala Tyr
145                 150                 155                 160

Gly Met Arg Ala Ala Gln Phe His Ala Arg Phe Met Asp Ala Ile Thr
                165                 170                 175

Pro Thr Gly Thr Val Ile Thr Leu Leu Gly Leu Thr Pro Glu Gly His
                180                 185                 190

Arg Val Ala Val His Val Tyr Gly Thr Arg Gln Tyr Phe Tyr Met Asn
            195                 200                 205

Lys Glu Glu Val Asp Arg His Leu Gln Cys Arg Ala Pro Arg Asp Leu
    210                 215                 220
```

-continued

```
Cys Glu Arg Met Ala Ala Ala Leu Arg Glu Ser Pro Gly Ala Ser Phe
225                 230                 235                 240

Arg Gly Ile Ser Ala Asp His Phe Glu Ala Glu Val Val Glu Arg Thr
            245                 250                 255

Asp Val Tyr Tyr Tyr Glu Thr Arg Pro Ala Leu Phe Tyr Arg Val Tyr
        260                 265                 270

Val Arg Ser Gly Arg Val Leu Ser Tyr Leu Cys Asp Asn Phe Cys Pro
    275                 280                 285

Ala Ile Lys Lys Tyr Glu Gly Gly Val Asp Ala Thr Thr Arg Phe Ile
290                 295                 300

Leu Asp Asn Pro Gly Phe Val Thr Phe Gly Trp Tyr Arg Leu Lys Pro
305                 310                 315                 320

Gly Arg Asn Asn Thr Leu Ala Gln Pro Ala Pro Met Ala Phe Gly
            325                 330                 335

Thr Ser Ser Asp Val Glu Phe Asn Cys Thr Ala Asp Asn Leu Ala Ile
            340                 345                 350

Glu Gly Gly Met Ser Asp Leu Pro Ala Tyr Lys Leu Met Cys Phe Asp
        355                 360                 365

Ile Glu Cys Lys Ala Gly Gly Glu Asp Glu Leu Ala Phe Pro Val Ala
370                 375                 380

Gly His Pro Glu Asp Leu Val Ile Gln Ile Ser Cys Leu Leu Tyr Asp
385                 390                 395                 400

Leu Ser Thr Thr Ala Leu Glu His Val Leu Leu Phe Ser Leu Gly Ser
            405                 410                 415

Cys Asp Leu Pro Glu Ser His Leu Asn Glu Leu Ala Ala Arg Gly Leu
            420                 425                 430

Pro Thr Pro Val Val Leu Glu Phe Asp Ser Glu Phe Glu Met Leu Leu
            435                 440                 445

Ala Phe Met Thr Leu Val Lys Gln Tyr Gly Pro Glu Phe Val Thr Gly
450                 455                 460

Tyr Asn Ile Ile Asn Phe Asp Trp Pro Phe Leu Leu Ala Lys Leu Thr
465                 470                 475                 480

Asp Ile Tyr Lys Val Pro Leu Asp Gly Tyr Gly Arg Met Asn Gly Arg
            485                 490                 495

Gly Val Phe Arg Val Trp Asp Ile Gly Gln Ser His Phe Gln Lys Arg
            500                 505                 510

Ser Lys Ile Lys Val Asn Gly Met Val Asn Ile Asp Met Tyr Gly Ile
            515                 520                 525

Ile Thr Asp Lys Ile Lys Leu Ser Ser Tyr Lys Leu Asn Ala Val Ala
530                 535                 540

Glu Ala Val Leu Lys Asp Lys Lys Asp Leu Ser Tyr Arg Asp Ile
545                 550                 555                 560

Pro Ala Tyr Tyr Ala Ala Gly Pro Ala Gln Arg Gly Val Ile Gly Glu
            565                 570                 575

Tyr Cys Ile Gln Asp Ser Leu Leu Val Gly Gln Leu Phe Phe Lys Phe
            580                 585                 590

Leu Pro His Leu Glu Leu Ser Ala Val Ala Arg Leu Ala Gly Ile Asn
            595                 600                 605

Ile Thr Arg Thr Ile Tyr Asp Gly Gln Gln Ile Arg Val Phe Thr Cys
610                 615                 620

Leu Leu Arg Leu Ala Asp Gln Lys Gly Phe Ile Leu Pro Asp Thr Gln
625                 630                 635                 640
```

-continued

Gly Arg Phe Arg Gly Ala Gly Glu Ala Pro Lys Arg Pro Ala Ala
            645                 650                 655

Ala Arg Glu Asp Glu Glu Arg Pro Glu Glu Gly Glu Asp Glu Asp
            660                 665                 670

Glu Arg Glu Glu Gly Gly Glu Arg Glu Pro Glu Gly Ala Arg Glu
            675                 680                 685

Thr Ala Gly Arg His Val Gly Tyr Gln Gly Ala Arg Val Leu Asp Pro
            690                 695                 700

Thr Ser Gly Phe His Val Asn Pro Val Val Phe Asp Phe Ala Ser
705                 710                 715                 720

Leu Tyr Pro Ser Ile Ile Gln Ala His Asn Leu Cys Phe Ser Thr Leu
                    725                 730                 735

Ser Leu Arg Ala Asp Ala Val Ala His Leu Glu Ala Gly Lys Asp Tyr
            740                 745                 750

Leu Glu Ile Glu Val Gly Gly Arg Arg Leu Phe Phe Val Lys Ala His
            755                 760                 765

Val Arg Glu Ser Leu Leu Ser Ile Leu Leu Arg Asp Trp Leu Ala Met
770                 775                 780

Arg Lys Gln Ile Arg Ser Arg Ile Pro Gln Ser Ser Pro Glu Glu Ala
785                 790                 795                 800

Val Leu Leu Asp Lys Gln Gln Ala Ala Ile Lys Val Val Cys Asn Ser
            805                 810                 815

Val Tyr Gly Phe Thr Gly Val Gln His Gly Leu Leu Pro Cys Leu His
            820                 825                 830

Val Ala Ala Thr Val Thr Thr Ile Gly Arg Glu Met Leu Leu Ala Thr
            835                 840                 845

Arg Glu Tyr Val His Ala Arg Trp Ala Ala Phe Glu Gln Leu Leu Ala
            850                 855                 860

Asp Phe Pro Glu Ala Ala Asp Met Arg Ala Pro Gly Pro Tyr Ser Met
865                 870                 875                 880

Arg Ile Ile Tyr Gly Asp Thr Asp Ser Ile Phe Val Leu Cys Arg Gly
            885                 890                 895

Leu Thr Ala Ala Gly Leu Thr Ala Val Gly Asp Lys Met Ala Ser His
            900                 905                 910

Ile Ser Arg Ala Leu Phe Leu Pro Pro Ile Lys Leu Glu Cys Glu Lys
            915                 920                 925

Thr Phe Thr Lys Leu Leu Leu Ile Ala Lys Lys Tyr Ile Gly Val
            930                 935                 940

Ile Tyr Gly Gly Lys Met Leu Ile Lys Gly Val Asp Leu Val Arg Lys
945                 950                 955                 960

Asn Asn Cys Ala Phe Ile Asn Arg Thr Ser Arg Ala Leu Val Asp Leu
            965                 970                 975

Leu Phe Tyr Asp Asp Thr Val Ser Gly Ala Ala Ala Leu Ala Glu
            980                 985                 990

Arg Pro Ala Glu Glu Trp Leu Ala Arg Pro Leu Pro Glu Gly Leu Gln
            995                 1000                1005

Ala Phe Gly Ala Val Leu Val Asp Ala His Arg Arg Ile Thr Asp
            1010                1015                1020

Pro Glu Arg Asp Ile Gln Asp Phe Val Leu Thr Ala Glu Leu Ser
            1025                1030                1035

Arg His Pro Arg Ala Tyr Thr Asn Lys Arg Leu Ala His Leu Thr
            1040                1045                1050

-continued

Val Tyr Tyr Lys Leu Met Ala Arg Arg Ala Gln Val Pro Ser Ile
1055                1060                1065

Lys Asp Arg Ile Pro Tyr Val Ile Val Ala Gln Thr Arg Glu Val
1070                1075                1080

Glu Glu Thr Val Ala Arg Leu Ala Ala Leu Arg Glu Leu Asp Ala
1085                1090                1095

Ala Ala Pro Gly Asp Glu Pro Ala Pro Pro Ala Ala Leu Pro Ser
1100                1105                1110

Pro Ala Lys Arg Pro Arg Glu Thr Pro Ser Pro Ala Asp Pro Pro
1115                1120                1125

Gly Gly Ala Ser Lys Pro Arg Lys Leu Leu Val Ser Glu Leu Ala
1130                1135                1140

Glu Asp Pro Ala Tyr Ala Ile Ala His Gly Val Ala Leu Asn Thr
1145                1150                1155

Asp Tyr Tyr Phe Ser His Leu Leu Gly Ala Ala Cys Val Thr Phe
1160                1165                1170

Lys Ala Leu Phe Gly Asn Asn Ala Lys Ile Thr Glu Ser Leu Leu
1175                1180                1185

Lys Arg Phe Ile Pro Glu Val Trp His Pro Pro Asp Asp Val Ala
1190                1195                1200

Ala Arg Leu Arg Thr Ala Gly Phe Gly Ala Val Gly Ala Gly Ala
1205                1210                1215

Thr Ala Glu Glu Thr Arg Arg Met Leu His Arg Ala Phe Asp Thr
1220                1225                1230

Leu Ala
1235

<210> SEQ ID NO 4
<211> LENGTH: 488
<212> TYPE: PRT
<213> ORGANISM: herpes simplex virus

<400> SEQUENCE: 4

Met Thr Asp Ser Pro Gly Gly Val Ala Pro Ser Pro Val Glu Asp
1                5                10                15

Ala Ser Asp Ala Ser Leu Gly Gln Pro Glu Glu Gly Ala Pro Cys Gln
                20                25                30

Val Val Leu Gln Gly Ala Glu Leu Asn Gly Ile Leu Gln Ala Phe Ala
        35                40                45

Pro Leu Arg Thr Ser Leu Leu Asp Ser Leu Leu Val Met Gly Asp Arg
    50                55                60

Gly Ile Leu Ile His Asn Thr Ile Phe Gly Glu Gln Val Phe Leu Pro
65                70                75                80

Leu Glu His Ser Gln Phe Ser Arg Tyr Arg Trp Arg Gly Pro Thr Ala
                85                90                95

Ala Phe Leu Ser Leu Val Asp Gln Lys Arg Ser Leu Leu Ser Val Phe
            100                105                110

Arg Ala Asn Gln Tyr Pro Asp Leu Arg Arg Val Glu Leu Ala Ile Thr
        115                120                125

Gly Gln Ala Pro Phe Arg Thr Leu Val Gln Arg Ile Trp Thr Thr Thr
    130                135                140

Ser Asp Gly Glu Ala Val Glu Leu Ala Ser Glu Thr Leu Met Lys Arg
145                150                155                160

Glu Leu Thr Ser Phe Val Val Leu Val Pro Gln Gly Thr Pro Asp Val
                165                170                175

-continued

```
Gln Leu Arg Leu Thr Arg Pro Gln Leu Thr Lys Val Leu Asn Ala Thr
            180                 185                 190
Gly Ala Asp Ser Ala Thr Pro Thr Thr Phe Glu Leu Gly Val Asn Gly
            195                 200                 205
Lys Phe Ser Val Phe Thr Ser Thr Cys Val Thr Phe Ala Ala Arg
            210                 215                 220
Glu Glu Gly Val Ser Ser Thr Ser Thr Gln Val Gln Ile Leu Ser
225                 230                 235                 240
Asn Ala Leu Thr Lys Ala Gly Gln Ala Ala Asn Ala Lys Thr Val
            245                 250                 255
Tyr Gly Glu Asn Thr His Arg Thr Phe Ser Val Val Asp Asp Cys
            260                 265                 270
Ser Met Arg Ala Val Leu Arg Arg Leu Gln Val Gly Gly Thr Leu
            275                 280                 285
Lys Phe Phe Leu Thr Thr Pro Val Pro Ser Leu Cys Val Thr Ala Thr
            290                 295                 300
Gly Pro Asn Ala Val Ser Ala Val Phe Leu Leu Lys Pro Gln Lys Ile
305                 310                 315                 320
Cys Leu Asp Trp Leu Gly His Ser Gln Gly Ser Pro Ser Ala Gly Ser
            325                 330                 335
Ser Ala Ser Arg Ala Ser Gly Ser Glu Pro Thr Asp Ser Gln Asp Ser
            340                 345                 350
Ala Ser Asp Ala Val Ser His Gly Asp Pro Glu Asp Leu Asp Gly Ala
            355                 360                 365
Ala Arg Ala Gly Glu Ala Gly Ala Leu His Ala Cys Pro Met Pro Ser
            370                 375                 380
Ser Thr Thr Arg Val Thr Pro Thr Thr Lys Arg Gly Arg Ser Gly Gly
385                 390                 395                 400
Glu Asp Ala Arg Ala Asp Thr Ala Leu Lys Lys Pro Lys Thr Gly Ser
            405                 410                 415
Pro Thr Ala Pro Pro Ala Asp Pro Val Pro Leu Asp Thr Glu Asp
            420                 425                 430
Asp Ser Asp Ala Ala Asp Gly Thr Ala Ala Arg Pro Ala Ala Pro Asp
            435                 440                 445
Ala Arg Ser Gly Ser Arg Tyr Ala Cys Tyr Phe Arg Asp Leu Pro Thr
            450                 455                 460
Gly Glu Ala Ser Pro Gly Ala Phe Ser Ala Phe Arg Gly Gly Pro Gln
465                 470                 475                 480
Thr Pro Tyr Gly Phe Gly Phe Pro
            485
```